(12) United States Patent
Rosenberg et al.

(10) Patent No.: US 10,951,597 B2
(45) Date of Patent: *Mar. 16, 2021

(54) METHODS AND SYSTEMS FOR TRANSFERRING SECURE DATA AND FACILITATING NEW CLIENT ACQUISITIONS

(71) Applicant: MEDICOM TECHNOLOGIES, INC., Raleigh, NC (US)

(72) Inventors: Michael Rosenberg, Raleigh, NC (US); Malcolm Benitz, Raleigh, NC (US); Chase Ballard, Raleigh, NC (US); Jason Suttles, Raleigh, NC (US); Chris Woodlief, Raleigh, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 16/281,409

(22) Filed: Feb. 21, 2019

(65) Prior Publication Data

US 2019/0190897 A1  Jun. 20, 2019

Related U.S. Application Data

(63) Continuation of application No. 15/361,320, filed on Nov. 25, 2016, now Pat. No. 10,305,869.

(Continued)

(51) Int. Cl.
| | |
|---|---|
| *H04L 29/06* | (2006.01) |
| *G16H 10/60* | (2018.01) |
| *G16H 30/20* | (2018.01) |
| *G16H 40/67* | (2018.01) |
| *H04L 12/58* | (2006.01) |

(Continued)

(52) U.S. Cl.
CPC .......... *H04L 63/0492* (2013.01); *G16B 50/00* (2019.02); *G16H 10/60* (2018.01); *G16H 30/20* (2018.01); *G16H 40/67* (2018.01); *G16H 50/70* (2018.01); *H04L 51/36* (2013.01); *H04L 63/0485* (2013.01); *H04L 63/061* (2013.01);

(Continued)

(58) Field of Classification Search
CPC . H04L 63/0492; H04L 51/36; H04L 63/0485; H04L 63/061; H04L 63/0876; H04L 67/06; H04L 67/42; H04L 63/08; H04L 63/10; G06F 19/00; G06F 19/30
USPC .......................................................... 713/170
See application file for complete search history.

(56) References Cited

U.S. PATENT DOCUMENTS

| | | | | |
|---|---|---|---|---|
| 5,910,987 A | * | 6/1999 | Ginter | G06F 21/10 |
| | | | | 348/E5.006 |
| 6,454,708 B1 | * | 9/2002 | Ferguson | A61B 5/02055 |
| | | | | 600/300 |

(Continued)

OTHER PUBLICATIONS

Thomas Kotmayr,"DTLS based security and two-way authentication for the Internet of Things", May 17, 2013, https://www.sciencedirect.com/science/article/pii/S1570870513001029 (Year: 2013).*

(Continued)

*Primary Examiner* — Shahriar Zarrineh

(57) ABSTRACT

Methods and systems for directly and securely transferring encrypted medical data between two remote locations, such as an imaging site and a diagnostic site, wherein the diagnostic site is not within a data transfer network utilized by the imaging site. The invention allows the diagnostic site to receive medical data and view the data using a thin client viewer, and allows the diagnostic site to register as an in-network site.

13 Claims, 20 Drawing Sheets

Related U.S. Application Data

(60) Provisional application No. 62/280,865, filed on Jan. 20, 2016.

(51) Int. Cl.
*H04L 29/08* (2006.01)
*G16B 50/00* (2019.01)
*G16H 50/70* (2018.01)

(52) U.S. Cl.
CPC .......... *H04L 63/0876* (2013.01); *H04L 67/06* (2013.01); *H04L 67/42* (2013.01)

(56) References Cited

U.S. PATENT DOCUMENTS

| | | | | |
|---|---|---|---|---|
| 6,557,102 B1* | 4/2003 | Wong | G06F 21/00 | 713/176 |
| 8,000,980 B2* | 8/2011 | Beraja | G06Q 50/22 | 705/2 |
| 8,108,432 B2* | 1/2012 | Westin | G06F 19/321 | 707/792 |
| 8,712,120 B1* | 4/2014 | Reicher | H04L 67/02 | 382/128 |
| 8,990,834 B2* | 3/2015 | Mathur | G06F 19/328 | 719/313 |
| 9,244,000 B2* | 1/2016 | Iyengar | G01N 21/7703 | |
| 2002/0010679 A1* | 1/2002 | Felsher | G06Q 20/3674 | 705/51 |
| 2002/0090119 A1* | 7/2002 | Saito | G16H 40/63 | 382/128 |
| 2002/0124177 A1* | 9/2002 | Harper | G06F 21/6245 | 713/189 |
| 2003/0188200 A1* | 10/2003 | Paquin | G06Q 10/10 | 726/4 |
| 2003/0206646 A1* | 11/2003 | Brackett | G06F 19/321 | 382/128 |
| 2004/0128163 A1* | 7/2004 | Goodman | G16H 40/20 | 705/2 |
| 2005/0114179 A1* | 5/2005 | Brackett | G06Q 10/10 | 705/2 |
| 2005/0275871 A1* | 12/2005 | Baird | H04L 12/2854 | 358/1.15 |
| 2006/0004588 A1* | 1/2006 | Ananda | G06Q 20/3674 | 705/67 |
| 2006/0242159 A1* | 10/2006 | Bishop | G06F 19/321 | |
| 2007/0135855 A1* | 6/2007 | Foshee | A61N 1/37252 | 607/31 |
| 2007/0185547 A1* | 8/2007 | Hoyme | G06F 19/3418 | 607/60 |
| 2007/0258626 A1* | 11/2007 | Reiner | G06Q 50/22 | 382/115 |
| 2008/0027752 A1* | 1/2008 | Phan | G06Q 50/22 | 705/2 |
| 2008/0221929 A1* | 9/2008 | Brackett | G06F 19/321 | 705/3 |
| 2009/0006850 A1* | 1/2009 | Birger | H04L 29/12207 | 713/169 |
| 2010/0010385 A1* | 1/2010 | Skelton | A61B 5/6846 | 600/595 |
| 2010/0299157 A1* | 11/2010 | Fram | G06Q 50/24 | 705/3 |
| 2010/0299517 A1* | 11/2010 | Jukic | H04L 12/2809 | 713/150 |
| 2011/0072519 A1* | 3/2011 | Apsel | G06F 21/64 | 726/27 |
| 2011/0153351 A1* | 6/2011 | Vesper | G06Q 50/22 | 705/2 |
| 2011/0161671 A1* | 6/2011 | Whitehouse | G06F 21/6236 | 713/171 |
| 2011/0320469 A1* | 12/2011 | Canessa | G16H 50/30 | 707/758 |
| 2012/0029303 A1* | 2/2012 | Shaya | A61B 5/0022 | 600/300 |
| 2012/0221535 A1* | 8/2012 | Dubbels | G06F 16/27 | 707/694 |
| 2012/0323590 A1* | 12/2012 | Udani | G16H 10/60 | 705/2 |
| 2013/0013921 A1* | 1/2013 | Bhathena | H04L 63/0471 | 713/168 |
| 2013/0129198 A1* | 5/2013 | Sherman | G16H 30/20 | 382/159 |
| 2013/0151286 A1* | 6/2013 | Kablotsky | G06F 19/321 | 705/3 |
| 2013/0297345 A1* | 11/2013 | Curry | G16H 10/60 | 705/3 |
| 2014/0142982 A1* | 5/2014 | Janssens | G06F 19/321 | 705/3 |
| 2014/0142984 A1* | 5/2014 | Wright | G06F 19/321 | 705/3 |
| 2014/0149512 A1* | 5/2014 | Leitch | H04L 67/1061 | 709/204 |
| 2014/0157370 A1* | 6/2014 | Plattner | H04L 63/1441 | 726/4 |
| 2014/0325035 A1* | 10/2014 | Ding | H04L 63/107 | 709/220 |
| 2015/0149565 A1* | 5/2015 | Ahmed | H04L 65/403 | 709/206 |
| 2015/0188956 A1* | 7/2015 | Chauhan | H04L 63/0861 | 726/7 |
| 2015/0264015 A1* | 9/2015 | Cialdea | G06F 19/321 | 726/26 |
| 2015/0288797 A1* | 10/2015 | Vincent | G16H 40/67 | 455/404.2 |
| 2015/0347464 A1* | 12/2015 | Takata | G16H 50/70 | 707/728 |
| 2015/0350251 A1* | 12/2015 | Brander | G06F 16/955 | 713/168 |
| 2015/0356271 A1* | 12/2015 | Kozuka | A61B 6/461 | 705/2 |
| 2015/0379209 A1* | 12/2015 | Kusuma | H04L 67/10 | 705/3 |
| 2016/0087933 A1* | 3/2016 | Johnson | H04W 12/0023 | 709/245 |
| 2016/0110265 A1* | 4/2016 | Athani | G06F 16/22 | 707/654 |
| 2016/0125152 A1* | 5/2016 | Higgs | G06F 19/3418 | 705/3 |
| 2016/0125162 A1* | 5/2016 | Takata | G16H 50/70 | 705/2 |
| 2016/0147952 A1* | 5/2016 | Garcia | G16H 10/60 | 705/3 |
| 2016/0155236 A1* | 6/2016 | Davey | G06T 7/33 | 382/131 |
| 2016/0246788 A1* | 8/2016 | Thangaraj | G06F 16/51 | |
| 2016/0301706 A1* | 10/2016 | Katz | H04L 63/1408 | |
| 2017/0054770 A1* | 2/2017 | Wells | H04L 65/1006 | |
| 2018/0103018 A1* | 4/2018 | Chauhan | H04L 63/168 | |
| 2020/0089897 A1* | 3/2020 | Shelton | G06F 16/27 | |

OTHER PUBLICATIONS

Y. Sheffer, Recommendations for Secure Use of Transport Layer Security(TLS) and Datagram Transport Layer Security(DTLS), Internet Engineering Task Force (IETF),Request for Comments: 7525, ISSN: 2070-1721, 26 pages https://tools.ietf.org/html/rfc7525 (Year: 2015).*

M.Tuexen, Datagram Transort Layer Security(DTLS) for stream Transmission Protocol(SCTP), Internet Engineering Task Force (IETF), Request for Comments: 6083, Category: Standards Track, ISSN: 2070-1721 https://www.hjp.at/doc/rfc/rfc6083.html (Year: 2011).*

* cited by examiner

METHODS AND SYSTEMS FOR TRANSFERRING SECURE DATA AND FACILITATING NEW CLIENT ACQUISITIONS

RELATED APPLICATIONS

This application claims the benefit of U.S. Non-Provisional patent application Ser. No. 15/361,320 entitled "METHODS AND SYSTEMS FOR TRANSFERRING SECURE DATA AND FACILITATING NEW CLIENT ACQUISITIONS" filed on Nov. 25, 2016, and U.S. Provisional Patent Application No. 62/280,865 entitled "METHOD, SYSTEM, AND DEVICE FOR PROVIDING SECURE AND AUDITABLE TRANSFER OF STUDIES BETWEEN CARE PROVIDER AND DIAGNOSTIC PROVIDER" filed on Jan. 20, 2016 which is commonly owned, the disclosures of which are incorporated herein by reference in its entirety.

BACKGROUND OF THE INVENTION

It is common place in today's environment to find medical care providers with an assortment of medical devices that produce digital images that need to be subsequently analyzed by specialist to identify potential health issues with the highest confidence. Examples fields making use of medical imaging would include radiology, cardiology imaging, and radiotherapy device (X-ray, CT, MM, ultrasound, etc.), and increasingly in devices in other medical domains such as ophthalmology and dentistry. Transmission of these images, or studies, are complicated by the fact that they are subject to HIPAA requirements, whereby all entities that take possession of the studies, even when ephemeral, must be pre-qualified as HIPAA compliant. One solution to this problem is to establish a VPN between the medical provider and the diagnostic lab. However, this solution suffers from complexity and cost. Installing a VPN between two providers commonly means segregating the network at both ends to limit what each of the other parties can see. While doing this between a single set of providers may seem straightforward, it quickly become less tractable when a single provider needs to communicate over VPN with a plurality of other providers. This means creating a separate zone for each of the other providers, and installing a separate VPN for each of the other providers.

Another popular method of transmitting the imaging data is to store it on a CD, DVD, or other media and mail through the postal system or other transportation provider. In previous years, when networks were generally slower, this method held appeal. However, it suffers from lack of immediacy given that it is generally quicker to send data over todays network than to suffer the delays in physical transit for all but the largest of transmissions. Physical media is also prone to being damaged, stolen, or lost in transit.

What is needed is a system that is quick and easy to install and configure, complies with all regulations regarding privacy and security, and provides for immediate delivery with confirmation and traceability.

SUMMARY OF THE INVENTION

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

According to one general aspect of the present invention includes a method for transferring data in a secure manner between a subscriber device and a non-subscriber device, comprising: transmitting, by the subscriber device, an electronic message to the non-subscriber device, wherein the electronic message includes an electronic link; receiving, by the non-subscriber device, the electronic message; downloading a viewer by the non-subscriber device, wherein the viewer is downloaded by accessing the electronic link; establishing, by the subscriber device, a communication channel with the non-subscriber device via the viewer; and transmitting an encrypted data package from the subscriber device to the non-subscriber device through the communication channel, wherein the subscriber device is registered with a data transfer network, and wherein the electronic link includes means for registering the non-subscriber device with the data transfer network.

In another general aspect the present invention includes a system for securely transmitting medical data to an out-of-network diagnostic provider, comprising: a medical provider device configured to transmit an electronic message containing an electronic link to download a viewer over a server; the diagnostic provider configured to receive the electronic message; the server configured to transmit the viewer to the diagnostic provider upon accessing the electronic link by the diagnostic provider, wherein the medical provider device is further configured to initiate a communication channel directly with the diagnostic provider via the viewer, wherein the medical provider device transmits a medical data package to the diagnostic provider via the communication channel, and wherein the communication channel is not coupled to the server, and wherein the electronic message further contains means for allowing the diagnostic provider to become an in-network diagnostic provider.

In another general aspect the present invention includes a system for transferring data in a secure manner between a subscriber device and a non-subscriber device, comprising: the subscriber device configured to transmit an electronic message containing an electronic link to download a viewer over a server; the non-subscriber device configured to receive the electronic message; the server configured to transmit the viewer to the non-subscriber device upon accessing of the electronic link by the non-subscriber device, wherein the subscriber device is further configured to initiate a communication channel directly with the non-subscriber device via the viewer, wherein the subscriber device transmits an encrypted data package to the non-subscriber device via the communication channel, and wherein the communication channel is not coupled to the server, and wherein the server is configured to store an audit trail related to the encrypted data package, and wherein the electronic message further contains means for allowing the non-subscriber device to register with the server, wherein registering with the server includes transmitting a payment authorization by the non-subscriber device to the server.

The system includes a first peer client, second peer client, and third server device all operable to communicate over a network. The first peer device may be operable to encrypt, using a first encryption key and a second encryption key, transmission payload data to produce an encrypted transmission payload; and send, to a second peer client, the encrypted transmission payload, wherein at no time during transmission is an entire copy of the encrypted transmission payload stored at an intermediate server in transmission to the second peer client. The second peer client may be operable to receive from the first peer client, the encrypted transmission payload; and decrypt, using the first encryption key and the second encryption key, the encrypted transmission payload to produce the transmission payload data. The third server device may be operable to enable the communication between a first device operating the first peer client and a second device operating the second peer client.

According to one general aspect of the present invention a system is provided. The system includes a first peer client, second peer client, and third server device all operable to communicate over a network. The first peer client may be operable to receive, from the third device, a second network address; send, to the second peer client, the first encryption key associated with the first peer client; and receive, from the second peer client, the second encryption key associated with the second peer client. The second peer client may be operable to receive from the first peer client, the first encryption key. The third server device may be operable to receive the second network address; receive, from the first peer client, a request for the second network address; and send, to the first peer client, the second network address.

According to one general aspect of the present invention a system is provided. The system includes a first peer client, second peer client, and third server device all operable to communicate over a network. The first peer client may be operable to receive the encrypted transmission payload data, the transmission payload data comprising: image information identifying one or more images; and patient information identifying a patient associated with the one or more images. The second peer client may be operable to store the encrypted transmission payload data, the transmission payload data comprising: the image information identifying the one or more images; and the patient information identifying the patient associated with the one or more images.

According to one general aspect of the present invention a system is provided. The system includes a first peer client, second peer client, and third server device all operable to communicate over a network. The first peer client may be operable to pack the transmission payload data by encapsulating the image information and the patient information. The second peer client may be operable to unpack the transmission payload data by decapsulating the image information and the patient information.

According to one general aspect of the present invention a system is provided. The system includes a first peer client, second peer client, and third server device all operable to communicate over a network. The first peer client may be operable to store audit information reflecting transmission of the encrypted transmission payload and a destination to which it was sent.

According to one general aspect of the present invention a system is provided. The system includes a first peer client, second peer client, and third server device all operable to communicate over a network. The first peer client may be operable to send, to a fourth device, notification indicating completion of sending of the encrypted transmission payload.

According to one general aspect of the present invention a system is provided. The system includes a first peer client, second peer client, and third server device all operable to communicate over a network. The second peer client may be operable to send, to a fifth device, notification indicating completion of a reception of the encrypted transmission payload.

According to one general aspect of the present invention a system is provided. The system includes a first peer client, second peer client, and third server device all operable to communicate over a network. The first peer client may be operable to send, to the third device, a second request for a directory; and receive, from the third device, the directory. The second peer client may be operable to enable registration of the second network address with the third device. The third server device may be operable to store, in the directory, the second network address associated with the second peer client; store, in the directory, a plurality of other network addresses associated with a plurality of other devices; and receive, from the first peer client, the second request for the directory.

According to one general aspect of the present invention a system is provided. The system includes a first device, second device, and third server device all operable to communicate over a network. The first device may be operable to execute the first peer client. The second device may be operable to execute the second peer client.

According to one general aspect of the present invention a system is provided. The system includes a first peer client, second peer client, and third server device all operable to communicate over a network. The first peer client may be operable to send, to the second peer client, an offer; and receive, from the second peer client, an offer response. The second peer client may be operable to receive, from the first peer client, the offer; and send, to the first peer client, the offer response.

According to one general aspect of the present invention a system is provided. The system includes a first peer client, second peer client, and third server device all operable to communicate over a network. The first peer client may be operable to send, to the second peer client, a plurality of candidates; and receive, from the second peer client, a response to the plurality of candidates. The second peer client may be operable to receive, from the first peer client, the plurality of candidates; and send, to the first peer client, the response to the plurality of candidates.

According to one general aspect of the present invention a system is provided. The system includes a first peer client, second peer client, and third server device all operable to communicate over a network. The first peer client may be operable to receive the one or more images from a sixth device, the sixth device operating one of a PACS server and a DICOM server. The second peer client may be operable to send the one or more images at a seventh device, the sixth device operating one of the PACS server and the DICOM server.

According to one general aspect of the present invention a system is provided. The system includes a first peer client, second peer client, and third server device all operable to communicate over a network wherein the first peer client is geographically located at a medical provider facility.

According to one general aspect of the present invention a system is provided. The system includes a first peer client, second peer client, and third server device all operable to communicate over a network wherein the first peer client is one of a browser and a desktop application.

According to one general aspect of the present invention a system is provided. The system includes a first peer client, second peer client, and third server device all operable to communicate over a network the first peer client is operable to execute a WebRTC protocol.

According to one general aspect of the present invention a system is provided. The system includes a first peer client, second peer client, and third server device all operable to communicate over a network wherein first peer client further comprises one of a PACS viewer and a DICOM viewer.

According to one general aspect of the present invention a system is provided. The system includes a first peer client, second peer client, and third server device all operable to communicate over a network wherein the second peer client is geographically located at a diagnostic provider facility.

According to one general aspect of the present invention a system is provided. The system includes a first peer client, second peer client, and third server device all operable to communicate over a network wherein the second peer client is one of a browser and a desktop application.

According to one general aspect of the present invention a system is provided. The system includes a first peer client, second peer client, and third server device all operable to communicate over a network wherein the one or more images comprising the encrypted transmission payload are sent in DICOM format.

According to one general aspect of the present invention a system is provided. The system includes a first peer client, second peer client, and third server device all operable to communicate over a network wherein the patient information comprising the encrypted transmission payload is sent in one or more formats chosen from a group consisting or plain text, XML, and a pdf.

According to one general aspect of the present invention a system is provided. The system includes a first peer client, second peer client, and third server device all operable to communicate over a network. The system may further include an eighth device operating as a first endpoint device. The first endpoint device may operate to receive first data stored at the first device; receive other data stored at another device; aggregate the first data and the other data; and provide to a ninth device one or more of the first data and the other data.

According to one general aspect of the present invention a system is provided. The system includes a first peer client, second peer client, and third server device all operable to communicate over a network. The system may further include an eighth device operable to mirror, at a second endpoint device, the other data.

According to one general aspect of the present invention a system is provided. The system includes a first peer client, second peer client, and third server device all operable to communicate over a network. The system may further include an eighth device operable to send to a first endpoint device, the first endpoint device storing desired information, a first network packet configured to determine one or more first network response characteristics between the third endpoint device and first endpoint device; record the one or more first network response characteristics; send to a second endpoint device, the second endpoint device storing the desired information, a second network packet configured to determine one or more second network response characteristics between the third endpoint device and second endpoint device; record the one or more first network response characteristics; perform a comparison of the one or more first network response characteristics to the one or more first network response characteristics; designate, based on the comparison, one of the first endpoint device and the second endpoint device as a source; and receive the data from the source the desired information.

According to one general aspect of the present invention a system is provided. The system includes a first peer client, second peer client, and third server device all operable to communicate over a network. The first peer client may be operable to receive input designating an e-mail address of an intended recipient; send, using the e-mail address, information configured to enable a recipient device to download a recipient peer client and receive the encrypted transmission payload; and the recipient device operable to download the recipient peer client; and receive the encrypted transmission payload.

According to one general aspect of the present invention a system is provided. The system includes a first peer client, second peer client, and third server device all operable to communicate over a network. The first peer client may be operable to present first information identifying a plurality of possible recipients; receive first input designating ones of the plurality of possible recipients as favorites; present second information identifying the favorites; and receive second input designating one of the favorites as an intended recipient.

According to one general aspect of the present invention a system is provided. The system includes a first peer client, second peer client, and third server device all operable to communicate over a network. The first peer client may be operable to receive first input designating a first rule configured to be executed upon sending of the encrypted transmission payload; and execute the first rule. The second peer client may be operable to receive second input designating a second rule configured to be executed upon reception of the encrypted transmission payload; and execute the second rule.

According to one general aspect of the present invention a system is provided. The system includes a first peer client, second peer client, and third server device all operable to communicate over a network. The first peer client may be operable to execute as a first background process, wherein the first background process is a first communications node. The second peer client may be operable to execute as a second background process, wherein the second background process is a second communications node.

According to one general aspect of the present invention a system is provided. The system includes a first peer client, second peer client, and third server device all operable to communicate over a network.

The third server device may be operable to receive, from the first peer client, first information identifying activities having occurred at the first peer client; store, at the third device, the first information; receive, from the second peer client, second information identifying activities having occurred at the second peer client; and store, at the third device, the second information.

While the present invention has been summarized in terms and language describing a system, it will be recognized that methods, devices, and non-transitory computer readable medium embodiments are disclosed within the application including features similar to those described above.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

Figure 5:
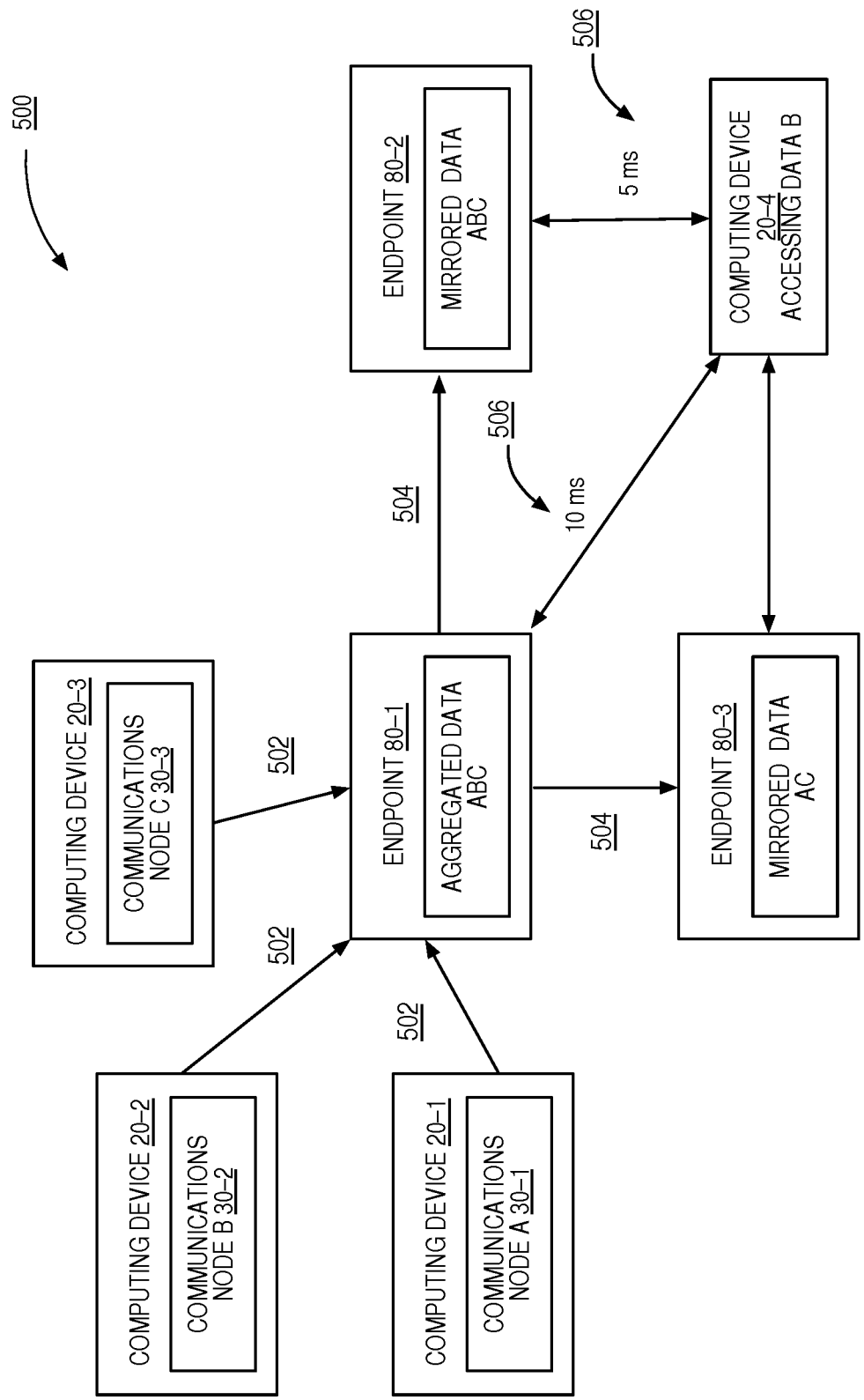
Figure 6:
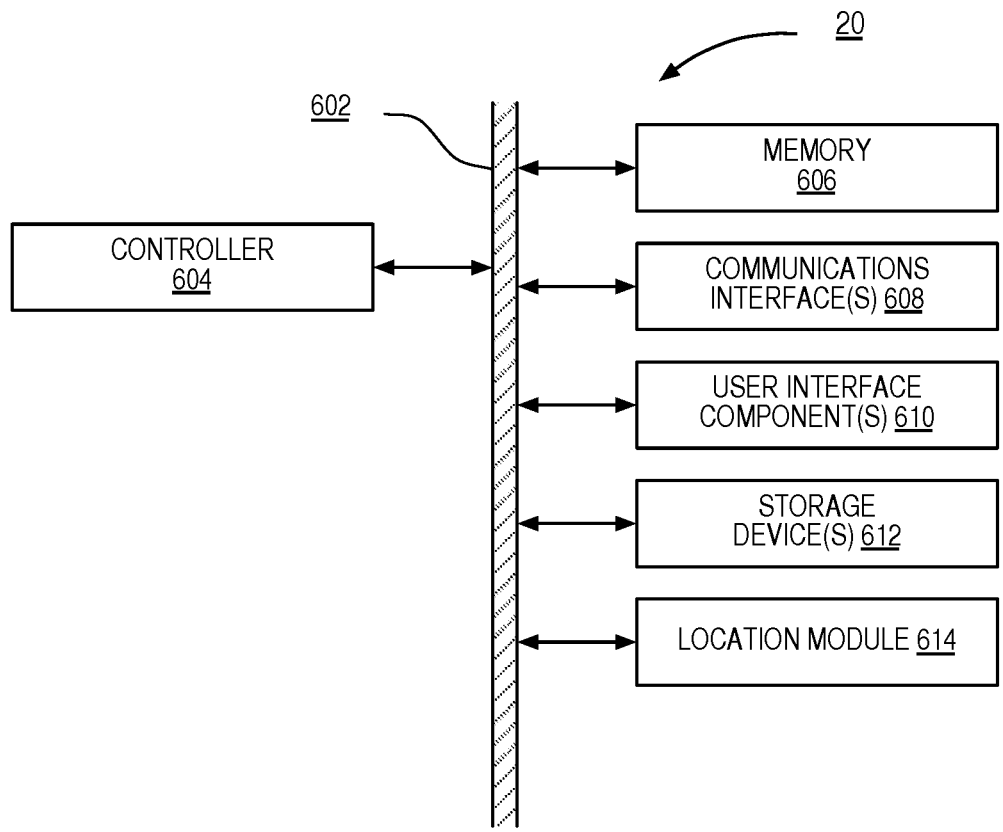
Figure 7:
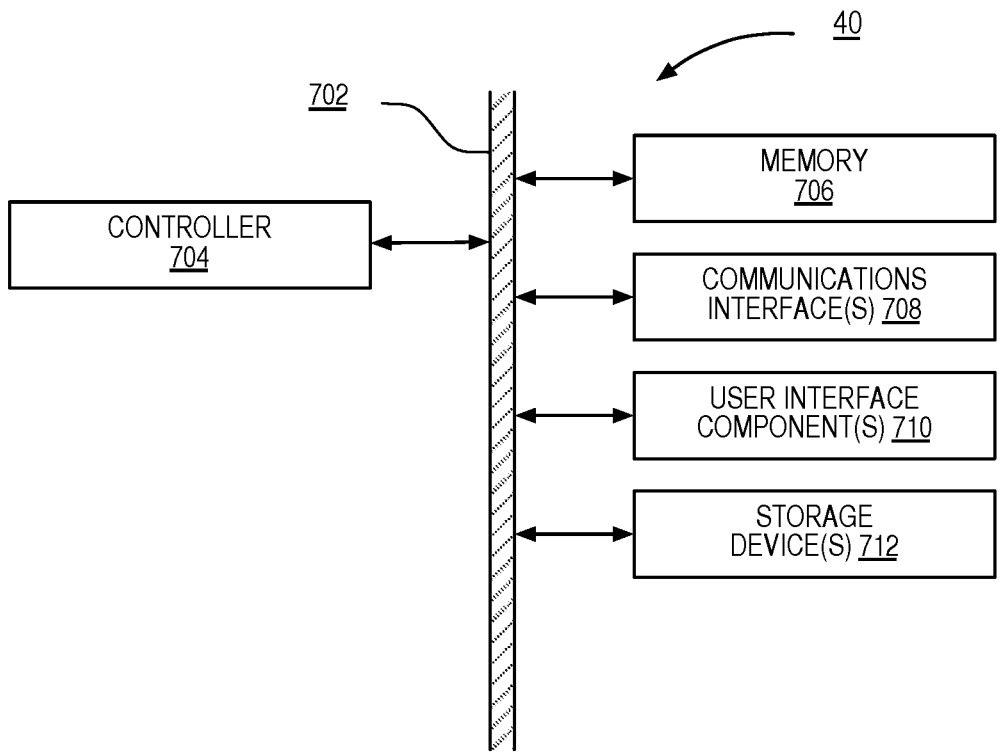
Figure 8:
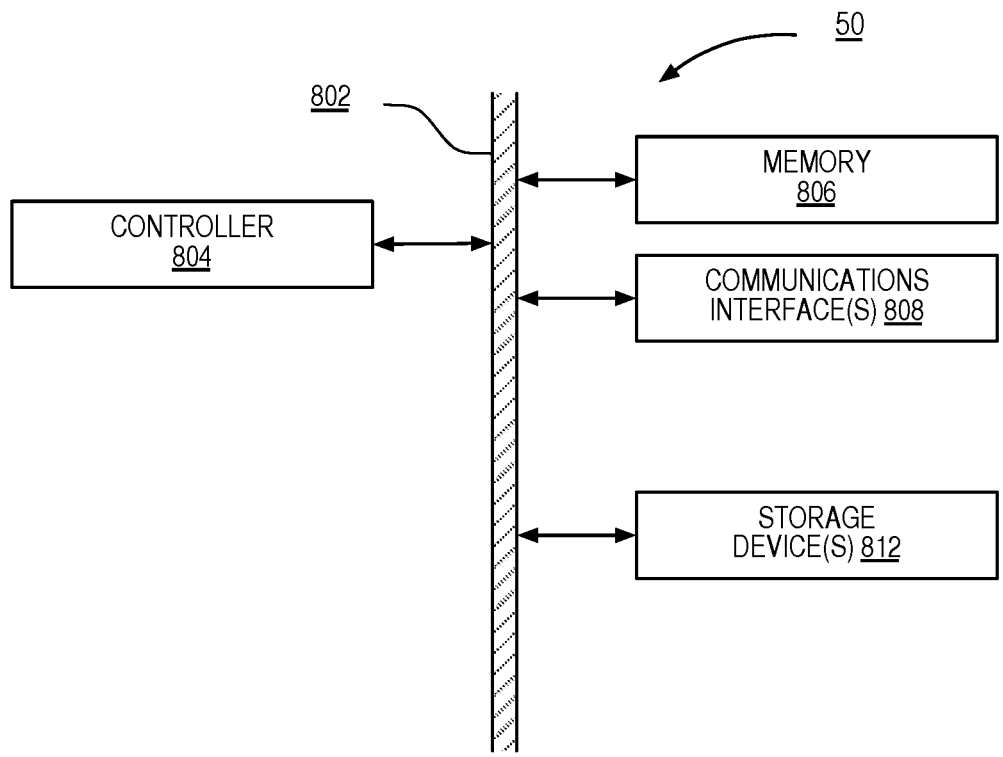
Figure 9:
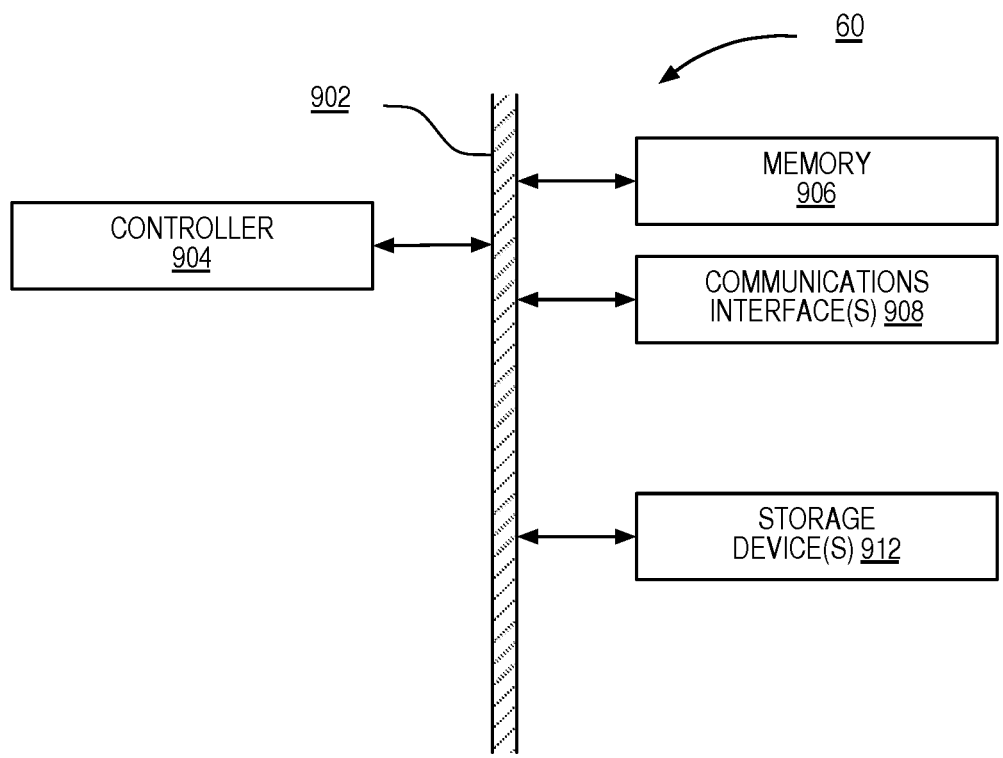
Figure 10:
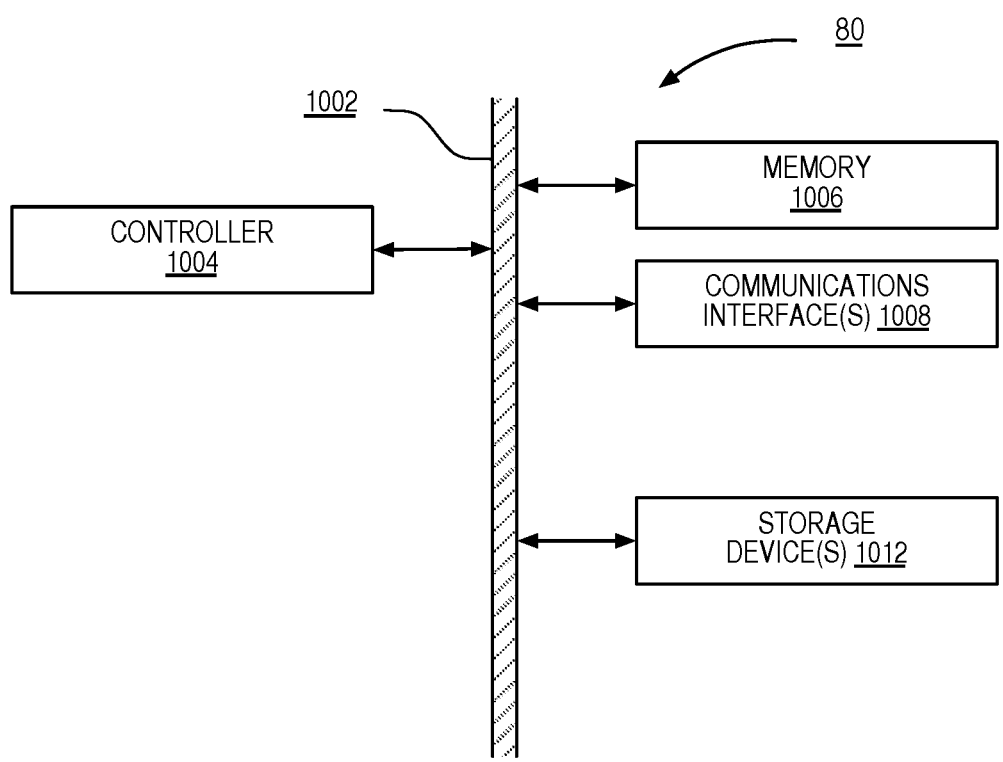

FIG. 5 graphically illustrates a system diagram of the operation of the endpoint device;

FIG. 6 graphically illustrates a block diagram of the hardware elements comprising the computing device;

FIG. 7 graphically illustrates a block diagram of the hardware elements comprising the content archival device;

FIG. 8 graphically illustrates a block diagram of the hardware elements comprising the web socket server device;

FIG. 9 graphically illustrates a block diagram of the hardware elements comprising the web server device; and FIG. 10 graphically illustrates a block diagram of the hardware elements comprising the endpoint device.

DETAILED DESCRIPTION

The present invention is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Throughout this specification, like reference numbers signify the same elements throughout the description of the figures.

When elements are referred to as being "connected" or "coupled," the elements can be directly connected or coupled together or one or more intervening elements may also be present. In contrast, when elements are referred to as being "directly connected" or "directly coupled," there are no intervening elements present.

The subject matter may be embodied as devices, systems, methods, and/or computer program products. Accordingly, some or all of the subject matter may be embodied in hardware and/or in software (including firmware, resident software, micro-code, state machines, gate arrays, etc.) Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store or transport the program for use by or in connection with the instruction execution system, apparatus, or device.

The computer-usable or computer-readable medium may be for example, but not limited to, an electronic, magnetic, optical, electromagnetic, semiconductor system, apparatus, or device. Computer storage media includes volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and may be accessed by an instruction execution system.

When the subject matter is embodied in the general context of computer-executable instructions, the embodiment may comprise program components, executed by one or more systems, computers, or other devices. Generally, program modules include routines, programs, objects, components, data structures, and the like, that perform particular tasks or implement particular abstract data types. Typically, the functionality of the program modules may be combined or distributed as desired in various embodiments.

Recitation of ranges of values herein are merely intended to serve as a shorthand method of referring individually to each separate value falling within the range, unless otherwise indicated herein, and each separate value is incorporated into the specification as if it were individually recited herein. Therefore, any given numerical range shall include whole and fractions of numbers within the range. For example, the range "1 to 10" shall be interpreted to specifically include whole numbers between 1 and 10 (e.g., 1, 2, 3, . . . 9) and non-whole numbers (e.g., 1.1, 1.2, . . . 1.9).

Although process (or method) steps may be described or claimed in a particular sequential order, such processes may be configured to work in different orders. In other words, any sequence or order of steps that may be explicitly described or claimed does not necessarily indicate a requirement that the steps be performed in that order unless specifically indicated. Further, some steps may be performed simultaneously despite being described or implied as occurring non-simultaneously (e.g., because one step is described after the other step) unless specifically indicated. Where a process is described in an embodiment the process may operate without any user intervention.

As referred to herein, the term "computing device" should be broadly construed. The computing device may employ operating environments in which embodiments of the present invention may be implemented are well-known. In a representative embodiment, a computing device may be a desktop computer, laptop computer, tablet computer, smart phones, and the like. The devices may employ well known operating environments or dedicated customized software. Examples of well-known operating environments include, but are not limited to, Microsoft Windows, Apple Macintosh System Software (OSX), Unix in any of its many flavors (RedHat Linux for example). Examples of well-known mobile operating environments include, but are not limited to, Apple iOS, RIM BlackBerry, Symbian, JavaVM (Android for example), webOS, Linux, Bada and the like.

Figure 1A:
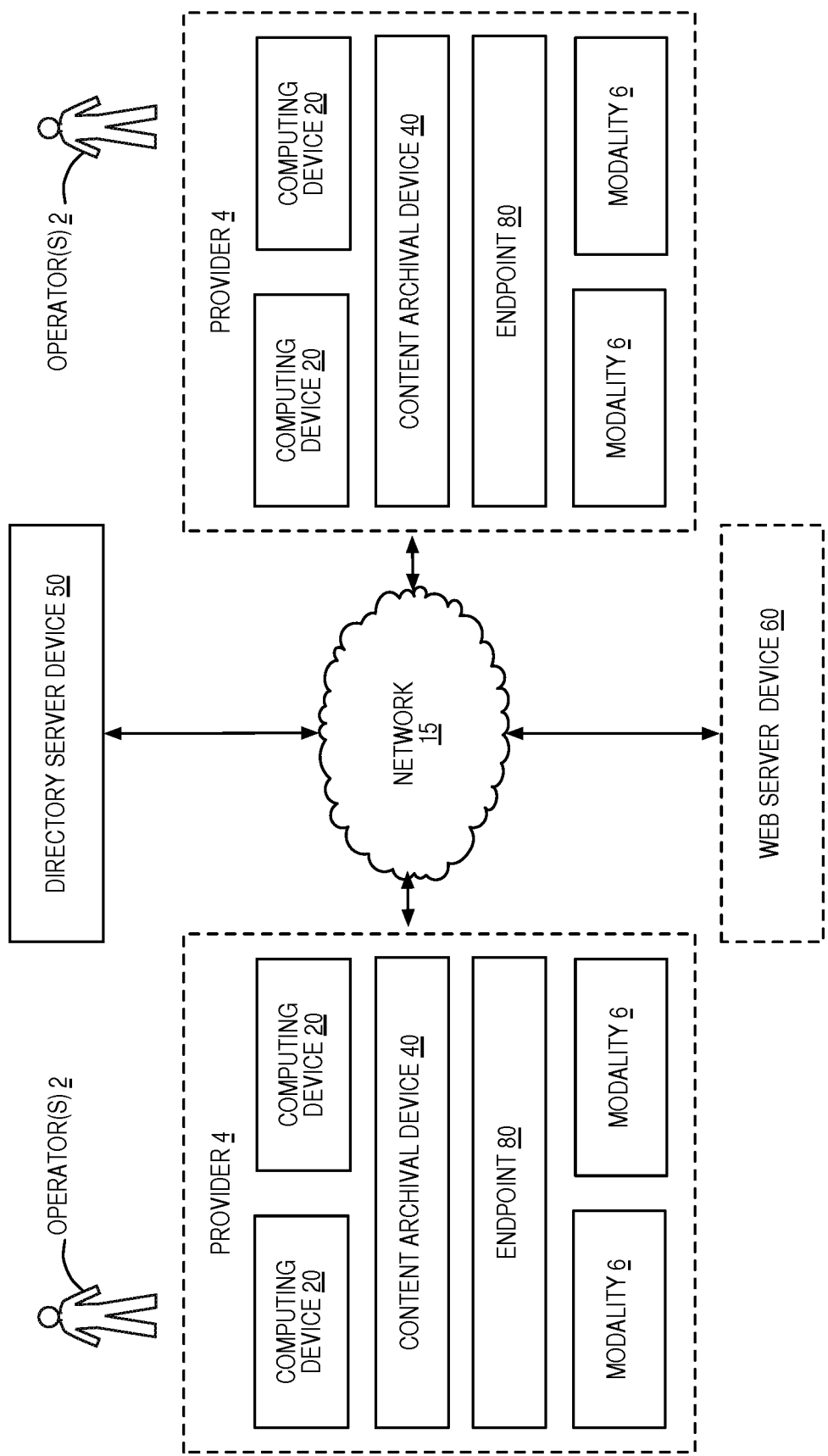
FIG. 1A illustrates a simplified system diagram for the system described in the present invention comprising a web socket server device, two or more computing devices, and two or more content archival devices.

FIG. 1A illustrates a simplified system diagram for the system described in the present invention comprising a web socket server device 50, web server device 60, and a plurality of providers 4, each of the providers 4 comprising a content archival device 40, a plurality of computing devices 20, an endpoint device 80, and a plurality of modalities 6. As used herein, a modality refers to a medical imaging device. Examples of modalities 6 include an Ultrasound Scanning device, a CT Scanning device, a X-Ray Scanning device, a DXA Scanning device, a PET Scanning device, and the like. The content archival device 40, the endpoint device 80, the plurality of computing devices 20, and the plurality of medical imaging devices 6 communicate with and through a local area network (not separately shown). Each provider 4 has one or more operators 2. The operators 2 may be doctors, nurses, technicians, office personnel, and the like. In general, a provider will be either a medical care provider or a diagnostic lab service provider. However, it is possible for a single provider to function in both capacities. Once connected, a computing device of the medical care provider operates as a peer client operable to communicate directly with a peer client of a second computing device of the diagnostic service provider and transfer data securely without the use of either VPNs or physical media. Further, the data is transferred without storing the data on any intermediate server.

In some implementations, the computing device 20 and the content archival device 40 are executed on the same physical machine or computing arrangement. In other instances, the computing device 20 and the content archival device 40 are operated on separate physically machines or computing arrangements.

As stated above, the network 15 is preferably a distributed, public access network, such as the Internet, wherein the computing device 20 and the web socket server device 50 are capable of interacting with and through the network 15 using various protocols such as Transmission Control Protocol/Internet Protocol (TCP/IP), Hypertext Transport Protocol (HTTP), and File Transfer Protocol (FTP). However, those of ordinary skill in the art will appreciate that the network 15 is not limited thereto. More specifically, the network 15 may be any type of network suitable to allow interaction between the computing devices 20 and the web socket server device 50. For example, the network 15 may be a wired network, a wireless network, or any combination thereof. Further, the network 15 may include a distributed computing network, an intranet, a local-area network (LAN) and/or a wide-area network (WAN), or any combination thereof. The network 15 may be comprised of wired and wireless elements. For example, the LAN may make use of WIFI in its many variations and the WAN may make use of cellular networks using technologies including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies.

Figure 1B:
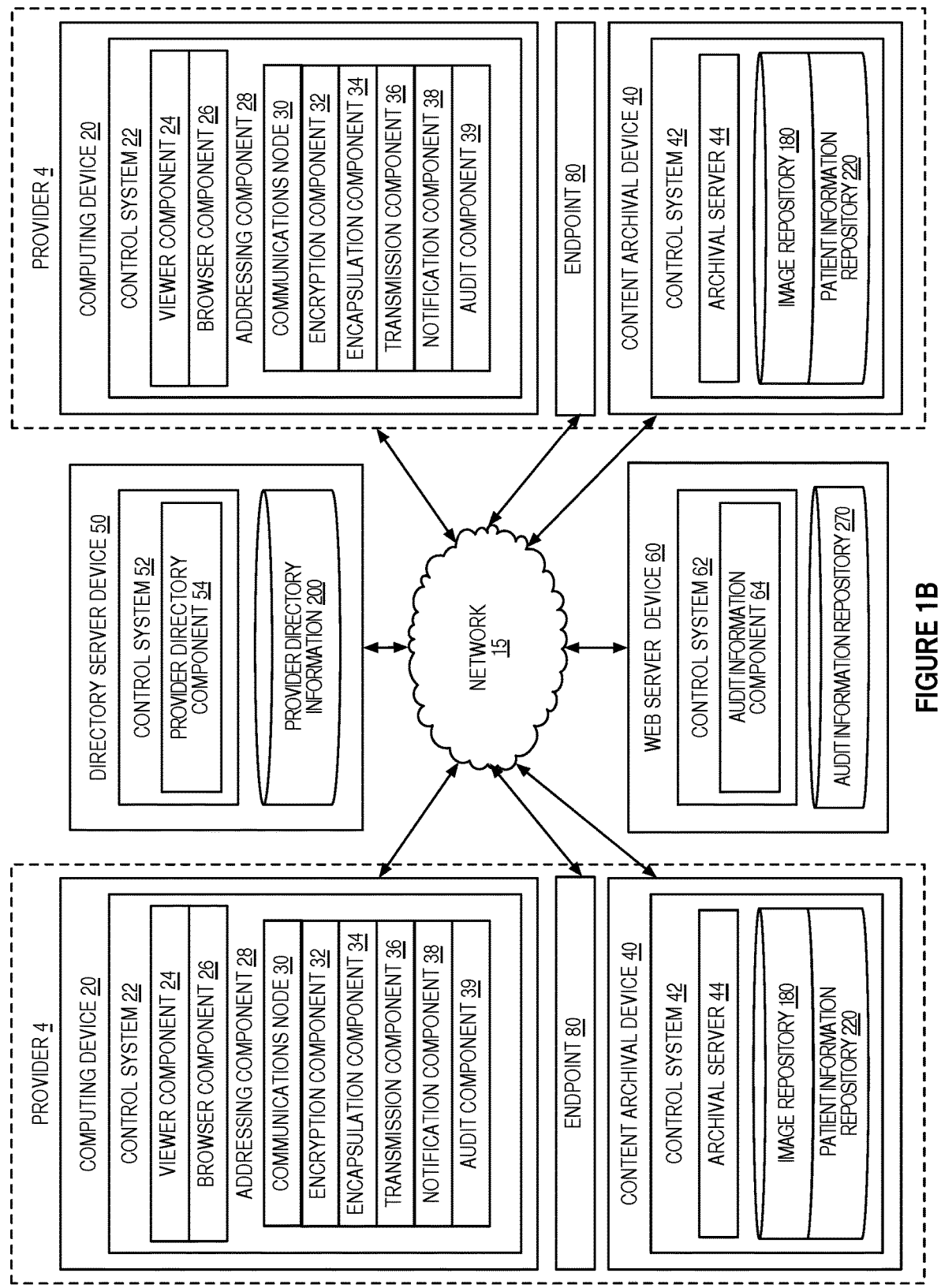
FIG. 1B illustrates the system described in the present invention comprising a web socket server device, two or more computing devices, and two or more content archival devices.

FIG. 1B illustrates the system described in the present invention comprising a web socket server device, and a plurality of providers. Each provider is comprised of a content archival device 40, an endpoint device 80, one or more computing devices 20, and one or more modalities 4. The computing device is comprised of a viewer component 24, browser component 26, and an addressing component 28. The viewer component 24 operates to allow an operator of the computing device 20 to access image information 290 and patient information 220 stored at the content archival device 40. The browser component 26 operates to allow the operator to communicate with the webserver present in the communications node 30. The addressing component 28 is invoked when a viewer application has a study ready for transmission. The viewer application sends the study to the communications node 30, which in turn triggers the addressing application. The addressing application then relays the study to the content archival device 40 and initiates the process of sending the study to the diagnostic lab service provider computing device 20. As used herein, a study refers to a collection of data comprising image data and patient data collected for detailed examination and analysis. The addressing node 28 is comprised of an communications node 30, encryption component 32, encapsulation component 34, transmission component 36, notification component 38, and audit component 40. The encryption component 32 is used to encrypt the image data 266 and patient data 268 to produce the encrypted data 264. The encapsulation component 34 operates to encapsulate the transmission payload 252 prior to transmission from the sending computing device to the receiving computing device by the transmission component 36. In some embodiments, the encapsulation is accomplished using a zip file. After sending the transmission payload, the notification component 38 sends notification to operator associated with the computing device. Finally, an audit entry 272 is added to the audit information repository 270. The content archival device 40 is comprised of an archival server 44. The archival server 44 communicates with one or more computing devices to provide access to the image repository 290 and the patient information repository 220. The image repository 290 stores image information and patient information, such as the patient information described in FIG. 2B. The web socket server device 50 is comprised of a provider directory component 64 and provider directory information 200, such as described in FIG. 2A. The web server device 60 is comprised of an audit information component 64 and audit information repository 270, such as described in FIG. 2D.

Figure 1C:
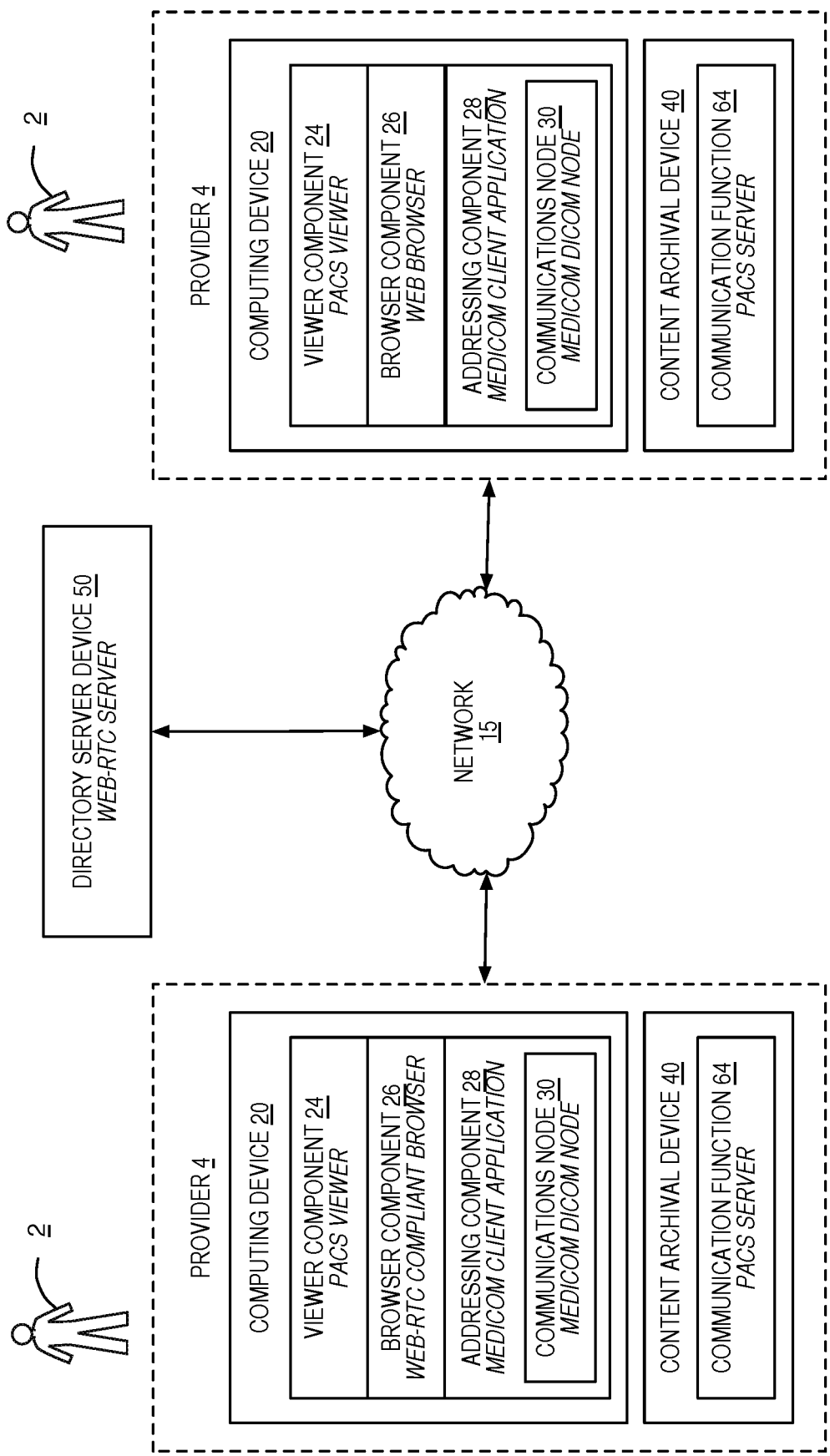
FIG. 1C illustrates one embodiment of the system described in FIGS. 1A and 1B.

FIG. 1C illustrates one embodiment of the system described in FIGS. 1A and 1B. In this particular embodiment, the viewer component 24 of the computing device 20 is implemented using a PACS viewer to provide element of the viewer component 24. A Web-RTC compliant browser 26 is used to provide the browser component 26. The addressing component 28 is provided by a PACS Client that is invoked automatically when a study is sent from the viewer component 24 to the communications node 30. The communications node 30 is implemented as a DICOM node.

As used herein, DICOM—Digital Imaging and Communications in Medicine—is the international standard for medical images and related information (ISO 12052). It defines the formats for medical images that can be exchanged with the data and quality necessary for clinical use. DICOM is implemented in almost every radiology, cardiology imaging, and radiotherapy device (X-ray, CT, MRI, ultrasound, etc.), and increasingly in devices in other medical domains such as ophthalmology and dentistry. With tens of thousands of imaging devices in use, DICOM is one of the most widely deployed healthcare messaging standards in the world.

As used herein, PACS—picture archiving and communication system—is a medical imaging technology which provides economical storage and convenient access to images from multiple modalities (source machine types). Electronic images and reports are transmitted digitally via PACS; this eliminates the need to manually file, retrieve, or transport film jackets. The universal format for PACS image storage and transfer is DICOM (Digital Imaging and Communications in Medicine). Non-image data, such as scanned documents, may be incorporated using consumer industry standard formats like PDF (Portable Document Format), once encapsulated in DICOM.

As used herein, Web-RTC (web real-time communications) is an emerging standard for enabling real-time peer-to-peer communications. While the stand is designed to meet the needs of real-time communications, it may also be adapted to send data that is not real-time in nature. Web-RTS makes use of a number of a number of standards and protocols. These include data streams, STUN/TURN servers, signaling, JSEP, ICE, SIP, SDP, NAT, UDP/TCP, network sockets, and the like.

Figure 1D:
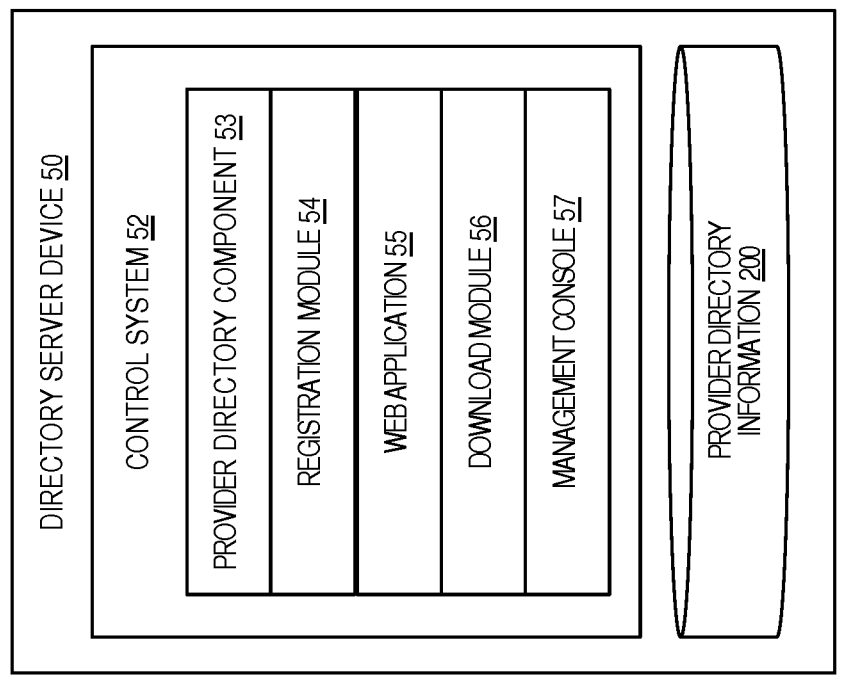
FIG. 1D illustrates an expanded view of the directory service device of FIG. 1A and FIG. 1B.

FIG. 1D illustrates an expanded view of the directory service device. The directory service device 50 is comprised of a control system 52, the control system 52 comprising provider directory component 54, registration module 55, web application 56, download module 57, management console 58, and a provider directory information 200. The registration module 55 operates to register providers 4 with the system. The web application 56 allows providers to interact with the directory service device 50 through various API's. The download module 57 allows providers 4 to download software to further operate with the directory service device 50. Software may include desktop applications, browser components 26, addressing components 28, endpoint device 80 software, and the like. The management console 58 operates to track actions taken by providers 4, such as sending and receiving encrypted transmission payloads. Additionally, the management console 58 provides for remote administration of various provider configuration and administration.

Figure 1E:
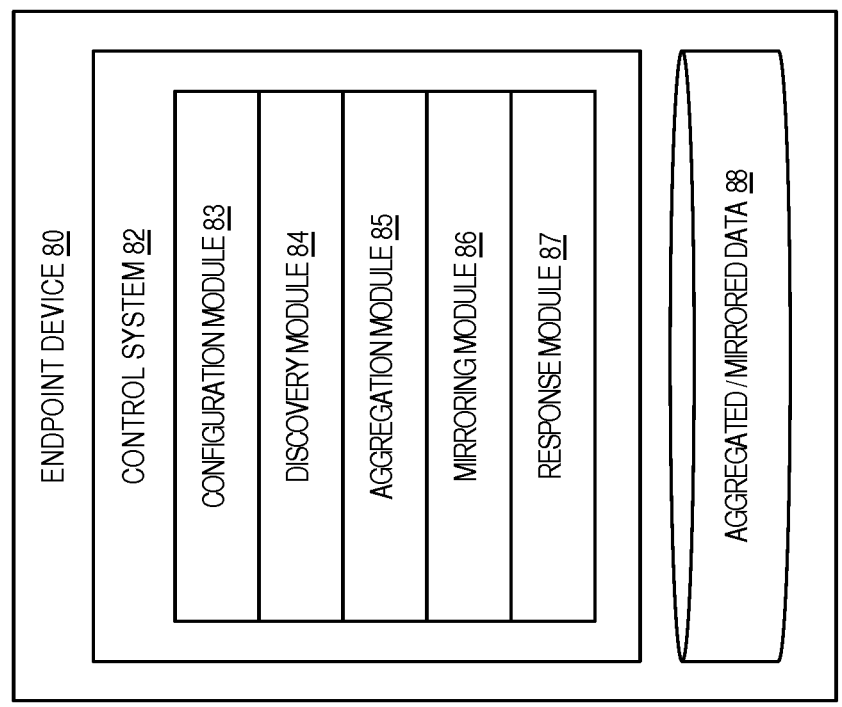
FIG. 1E illustrates an expanded view of the endpoint device of FIG. 1A and FIG. 1B.

FIG. 1E illustrates an expanded view of the endpoint device. The endpoint device 80 is comprised of control system 82, the control system 82 further comprising a configuration module 83, discovery module 84, aggregation module 85, mirroring module 86, and a response module 87. The configuration module 83 operates to allow the setting of configuration information for the endpoint device 80. The discovery module 84 operates to detect other devices enabled to interoperate with the endpoint device 80, such as other endpoint devices, and data sources, data sources including but not limited to viewer components 24, browser components 26, addressing components 28, communications nodes 30, and the like. The aggregation module 85 operates to aggregate data available at the previously described data sources. The mirroring module 86 operates to make the aggregated data available to other endpoint devices 80. The response module 87 operates to respond to ping messages used to identify endpoint devices with the lowest latency and the highest throughput.

Figure 2A:
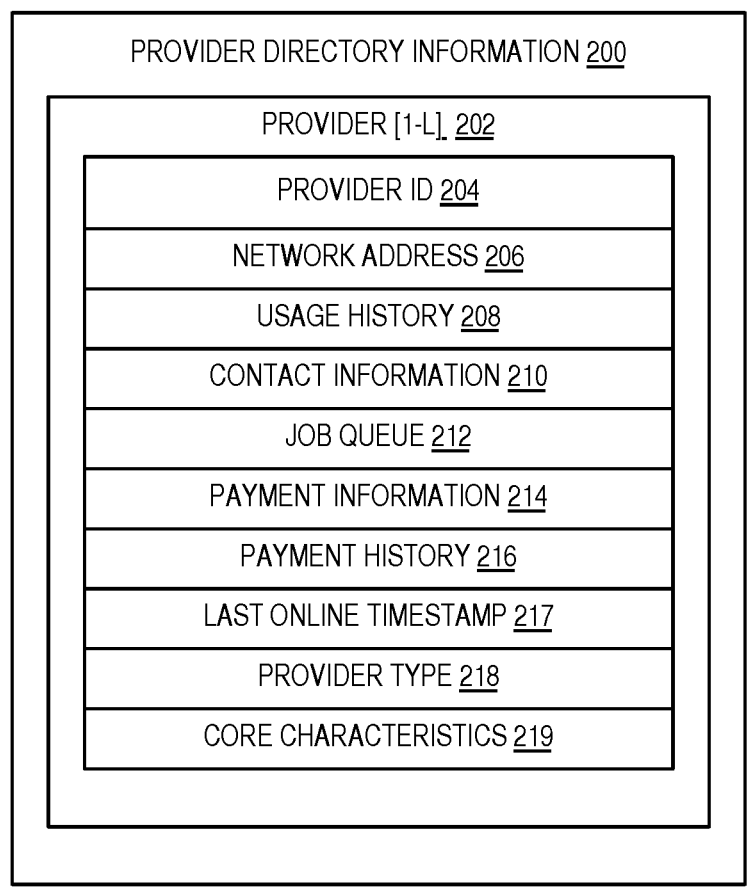
FIG. 2A illustrates an exemplary data structure for storing provider information according to some embodiments.

Referring now to FIG. 2A, the provider directory information 200 structure is comprised of a number of providers 202. Each provider structure is comprised of a provider ID 204, uniquely identifying the provider. The network address 206 is the address of the computing device being operated by the provider, if the computing device is on and connected to the web socket server device. In some embodiments the network address is the external IP address of the computing device. The usage history 208 is used to record the activity of the provider. The usage history may be used to record the information indicating when the provider account was created, when the provider has been connected to the system, and transactions that have been completed by the provider. The contact information 210 comprises information that can be used to contact the provider, included but not limited to, phone numbers, physical mailing address, e-mail address, twitter ID, chat address, etc. The job queue 212 contains information regarding jobs that have been initiated by the provider, but not completed, and require further action to complete. This may include jobs that have been schedule for a diagnostic provider computing device that is not connected to the web socket server device, and thus is not currently addressable and not able to receive and process the job at the present moment. The payment information 214 is used to store information enabling the web socket server device to process payment. Payments may be collected for using the system of FIG. 1A. Billing may be based on a recurring fee, a one-time seat license, per transaction, etc. The payment history 216 stores information on the various payments that have been collected. The last online timestamp 217 stores information indicating when the computing device corresponding to the provider 202 was last connected to the web socket server device. The provider type 218 indicates the type of the provider. Provider types 219 include medical care provider and diagnostic lab service provider.

Figure 2B:
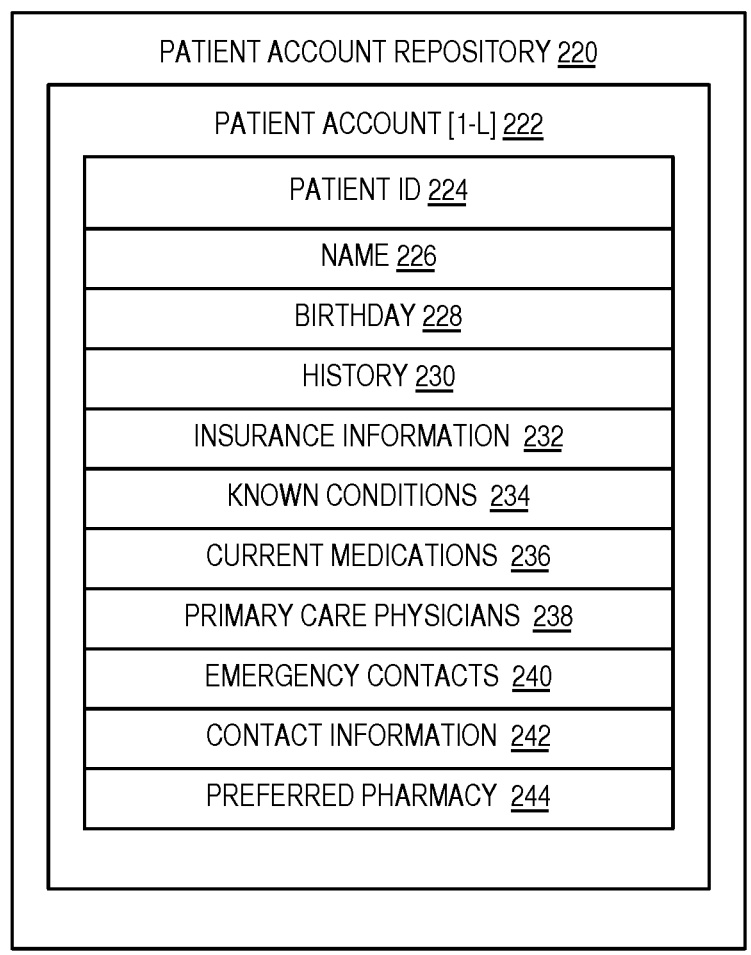
FIG. 2B illustrates an exemplary data structure for storing patient information according to some embodiments.

Referring now to FIG. 2B, the patient information 220 repository is comprised of any number of patient information 222 records. The patient ID 224 is a unique identifier identifying the patient within the system of FIG. 1. Patient name 226 stores the given name of the patient and patient birthday 228 stores the date of birth of the patient. Patient History 230 stores information regarding past ailments and treatments of the patient. Insurance information 232 stores information indicating the current insurance providers for the patient. Known conditions 234 store information identifying any number of known patient conditions. Current medications 236 store information identifying current medications that the patient is taking, including application instructions and dosages. Primary care physician 238 stores information identifying the primary care physician. Emergency contacts 240 stores information identifying and enabling contact of any number of emergency contacts. Patient contact information 242 stores information enabling contact of the patient such as phone numbers, physical mailing address, e-mail address, twitter ID, chat address, etc.

Preferred pharmacy 244 stores information identifying the pharmacy where the patient prefers to have prescriptions filled.

Figure 2C:
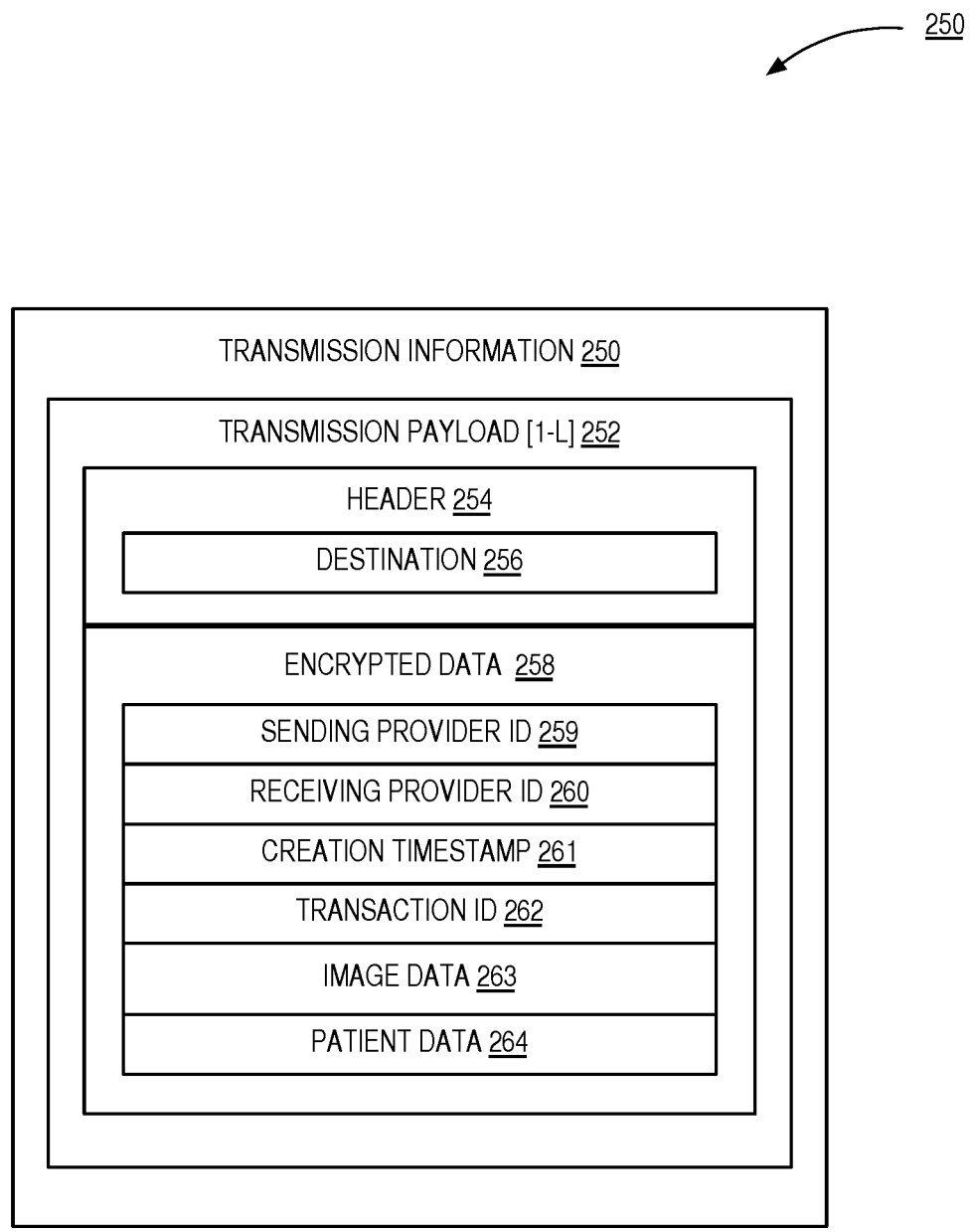
FIG. 2C illustrates an exemplary data structure for storing transmission payload information according to some embodiments.

Referring now to FIG. 2C, the transmission payload 250 structure comprises any number of transmission payloads 252. The transmission payload 252 is comprised of a header 254 and encrypted data 264. The header is comprised of a destination address 256. The encrypted data 258 is comprised of sending provider ID 259, receiving provider ID 260, a creation timestamp 261, transaction ID 262, image data 263 and patient data 264. The sending provider id 259 stores the identifier for the provider sending the transmission payload while the receiving provider id 260 stores the identifier for the provider receiving the transmission payload. The creation timestamp 261 stores the time and date that the transmission payload was created. The transaction ID 262 is a unique ID identifying the transaction within the system. The image data 263 contains the actual image data. The patient data 264 contains information about the patient. In some embodiments, the transmission payload image data and patient data are encapsulated prior to transmission. In some embodiments, this encapsulation is accomplished using a zip file to create a single binary file. In some embodiments, the transmission payload may be encrypted and transmitted using security technologies including but not limited to 2048 DTLS (Datagram Transport Layer Security) and 2048 RSA. RSA is one of the first practical public-key cryptosystems and is widely used for secure data transmission. In such a cryptosystem, the encryption key is public and differs from the decryption key which is kept secret. In RSA, this asymmetry is based on the practical difficulty of factoring the product of two large prime numbers. The encrypted data is signed using a hash created using the senders private key and the receivers public key enabling the receiver to verify the sender of the data. In some embodiments, the patient information is stored and transferred in the metadata of the DICOM images.

Figure 2D:
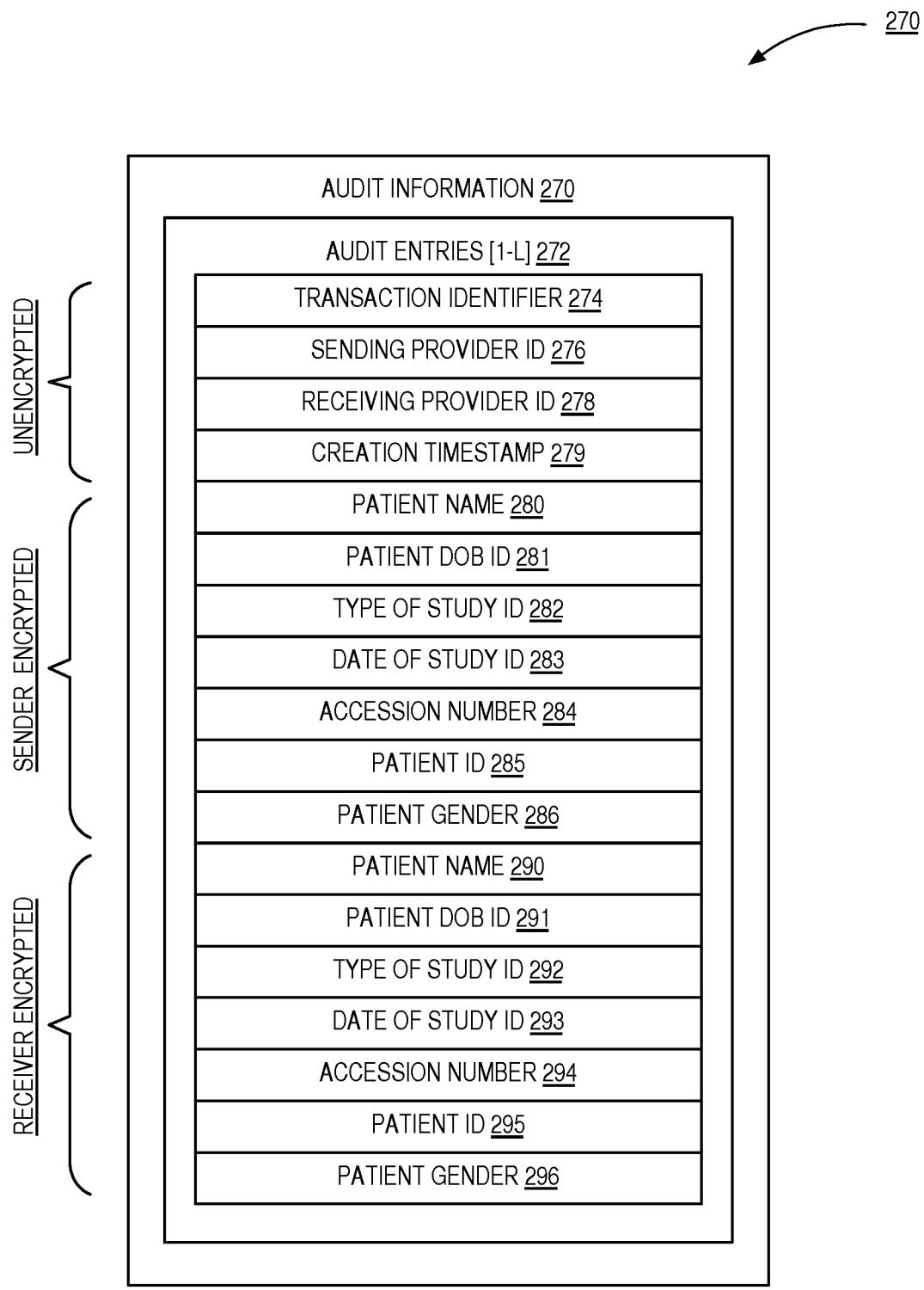
FIG. 2D illustrates an exemplary data structure for storing audit information according to some embodiments.

Referring now to FIG. 2D, the audit information 270 structure is comprised of one or more audit entries 272. An audit entry 272 is comprised of three sections. A first section, elements 274-279, are unencrypted. A second section, comprising elements 280-286, is encrypted using the sender key. A third section, comprising elements 290-296, is encrypted using the receiver key. The unencrypted elements are comprised of a transaction identifier 274, a sending provider id 276, and a receiving provider id 278, and a creation timestamp 279. The transaction identifier 274 uniquely identifies the transaction within the system of FIG. 1. The sender encrypted section is comprised of a patient name 280, a patient date of birth 281, the type of study 282, the date of the study 283, an accession number 284, a patient identifier 285, and the patient gender 286. The receiver encrypted section is comprised of a patient name 290, a patient date of birth 291, the type of study 292, the date of the study 293, an accession number 294, a patient identifier 285, and the patient gender 286.

The creation timestamp 280 indicates when the audit entry was created. Patient data shared 282 identifies the information that was transmitted in the transmission payload. Images shared 284 identifies the one or more images what were transmitted in the transmission payload. The transaction id 286 uniquely identifies the transaction within the system of FIG. 1.

Figure 3A:
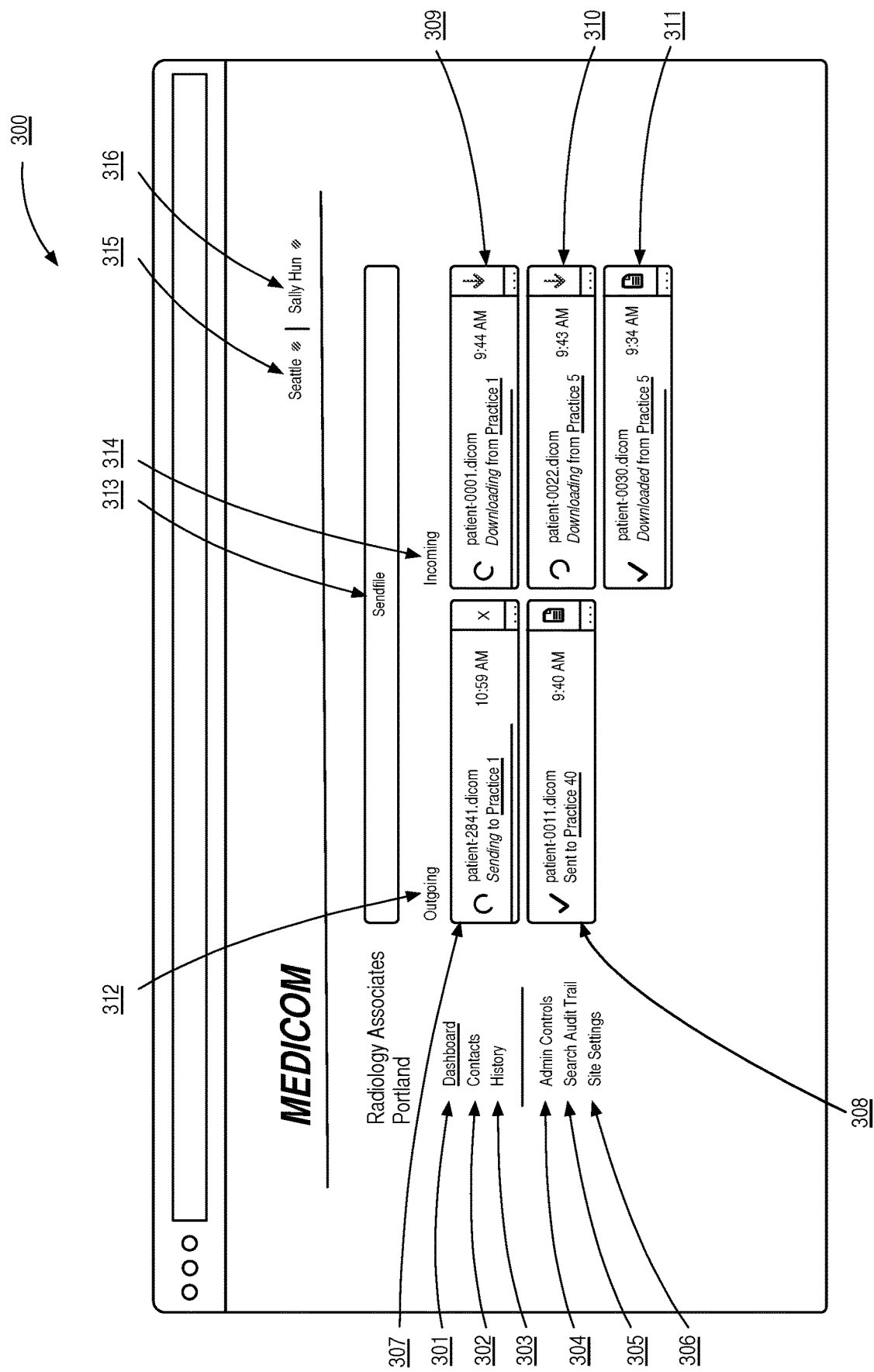
FIG. 3A illustrates a graphical browser user interface according to some embodiments.

FIG. 3A illustrates a graphical browser user interface according to some embodiments of the present invention. In this embodiment, the functionality of the computing device is exposed through a web browser application. The dashboard URL 301, when selected, operates to display the status on both incoming and outgoing studies. The contacts URL 302, when selected, operates to display a list of other computing devices corresponding to other providers. The list may include all other providers with which the provider has done business, a list of favorite other providers, a list of all other providers, a list of other providers currently online and available for immediate interaction, and the like. The history URL 303, when selected, operates to display information about past transaction and file transfers. The administrator control URL 304, when selected, operates allow the operator to provide inputs defining operator name, provider name, provider location, and the like. The audit trail control URL 305, when selected, operates to display the information on previously completed studies. In some embodiments, the audit information is comprised of the audit information shown in FIG. 2D. The audit information contains PHI (Patient History Information) as dictated by the HIPAA guidelines. This is only available to operators who have access to the specific encryption key that decrypts the audit information. The history does not contain PHI, so it can be viewed by anyone to view the success of file transfers without interacting with Patient Information.

The site settings control URL 306, when selected, operates to enable configuration of the communications node 30 with which browser component interacts. In one embodiment, such as the embodiment of FIG. 1C, the configuration is comprised of setting the AE Title and Ports.

Controls 307-311 are presented when the dashboard control 306 is selected. The outgoing study progress indicator 307 operates to present the status of an outgoing study still in the process of sending. The outgoing study progress indicator 308 operates to present the status of an outgoing study that has finished sending. The incoming study progress indicators 309 and 310 operates to present the status of an incoming study still in the process of reception. The outgoing study progress indicator 311 operates to present the status of an incoming study that has finished reception. The outgoing study column indicator 312 marks the display of outgoing studies. The sendfile URL selector 313, when selected, operates to send a study to a destination computing device. The incoming study column indicator 314 marks the display of incoming studies. The location indicator 315 operates to display the geographical location of the provider. The operator indicator 316 operates to display the name of the provider currently logged into the browser.

Figure 3B:
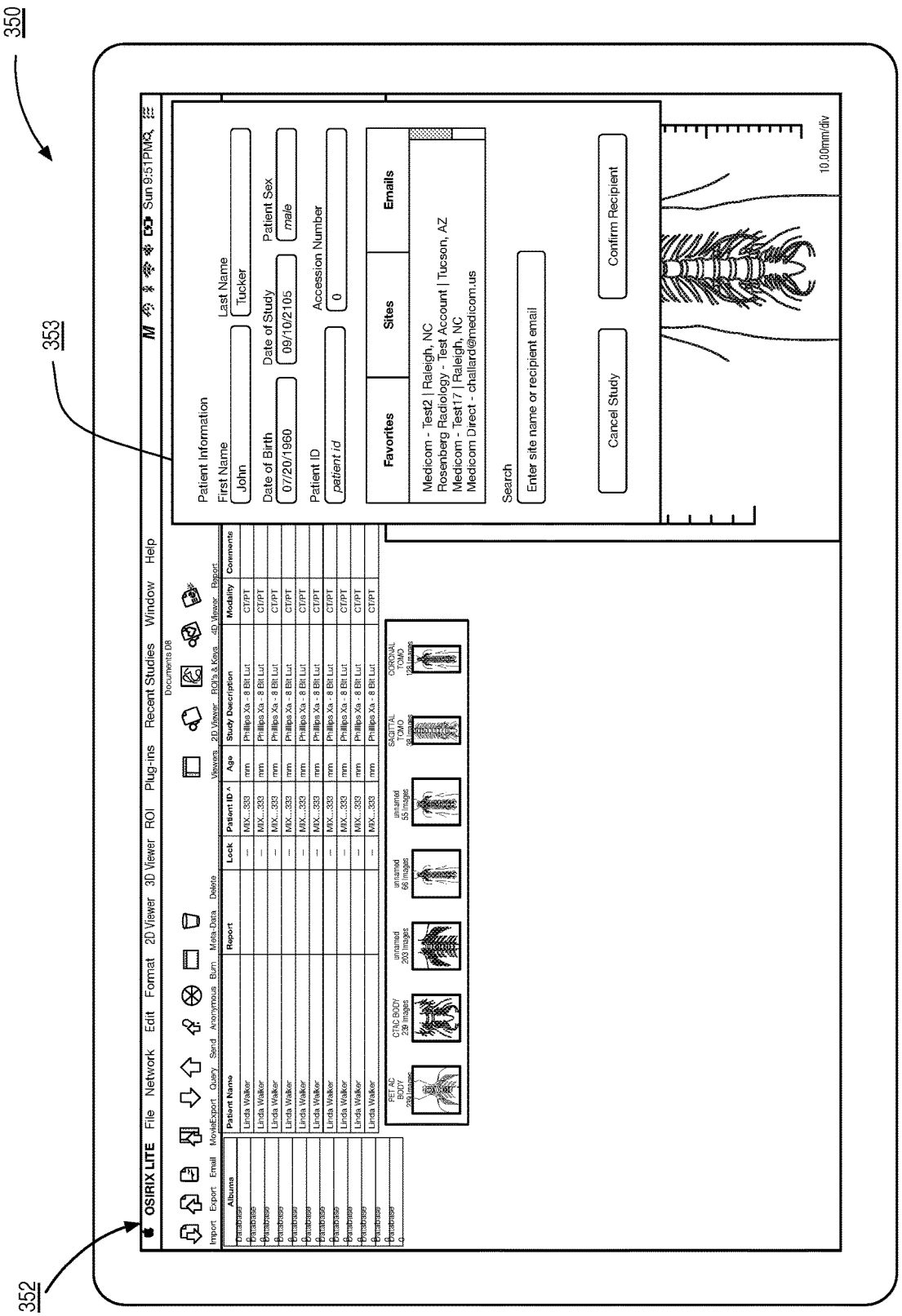
FIG. 3B illustrates a graphical desktop user interface according to some embodiments.

FIG. 3B illustrates graphical desktop user interface according to some embodiments. In this embodiment, the functionality of the computing device is exposed through a desktop application. In some embodiments, such as the embodiment of FIG. 1C, the desktop application is a PACS Viewer. The PACS Viewer provide an interface by which the operator defines the contents of a study, comprising the patient information and image information. Once the study is defined, the addressing application is invoked and the operator may provide the necessary inputs to address the study to another provider.

Figure 3C:
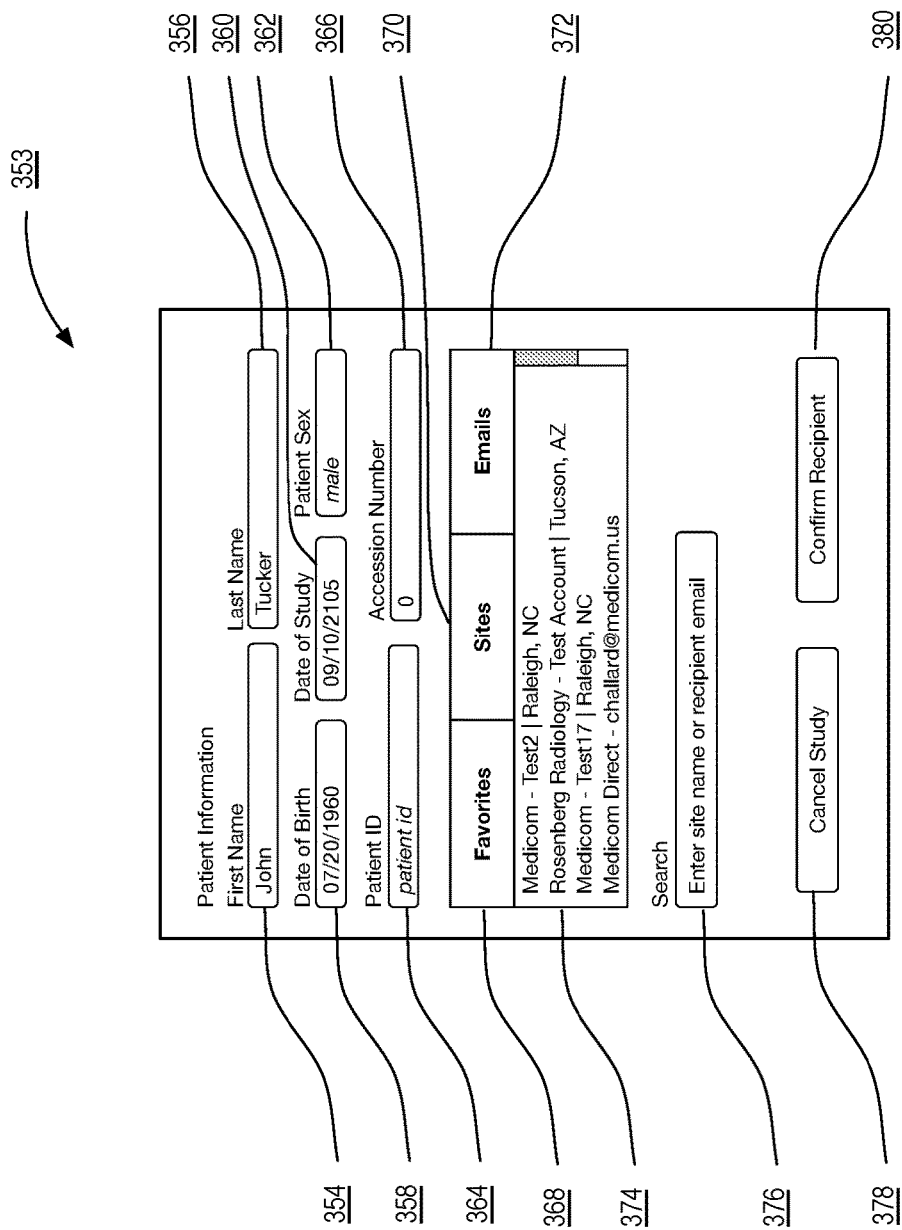
FIG. 3C illustrates a graphical user interface for entering patient and recipient information according to some embodiments.

Referring now to FIG. 3C, the first name text entry box 354 operates to allow the entry of the first name of the patient. The last name text entry box 356 operates to allow the entry of the last name of the patient. The date-of-birth text entry box 358 operates to allow the entry of the date-of-birth of the patient. The date-of-study text entry box 360 operates to allow the entry of the date-of-birth of the patient. The patient sex down menu box 362 operates to allow the entry of the date-of-birth of the patient. The patient identifier text entry box 364 operates to allow the entry of a unique identifier representing the patient. The accession number text entry box 366 operates to allow the entry of a accession number. The Favorites menu tab 368 allows the selection of a destination computing device for the study from among destinations that have been designated as favorites. Favorites may represent frequently used destinations. The Sites menu tab 370 allows browsing among all available sites. The Emails menu tab 372 allows for the delivery of a study through the use of e-mail. The email recipient will receive an e-mail comprising information indicating the availability of a study and providing directions to download and install the necessary software to receive and operate on the study. The search box 376 allows for the searching of all available sites and e-mail addresses. Once complete, they operate may elect to cancel transmission of the study 378, or to confirm and send 380 the study to the selected destination computing device. In some embodiments, such as the embodiment of FIG. 1C, the addressing application scrapes the DICOM image file to extract this information and automatically populates the items in the dialog box 353.

In some embodiments, such as the embodiment of FIG. 1C, the viewer component 24 and addressing component 28 communicate with and through the DICOM Node 30.

Figure 4A:
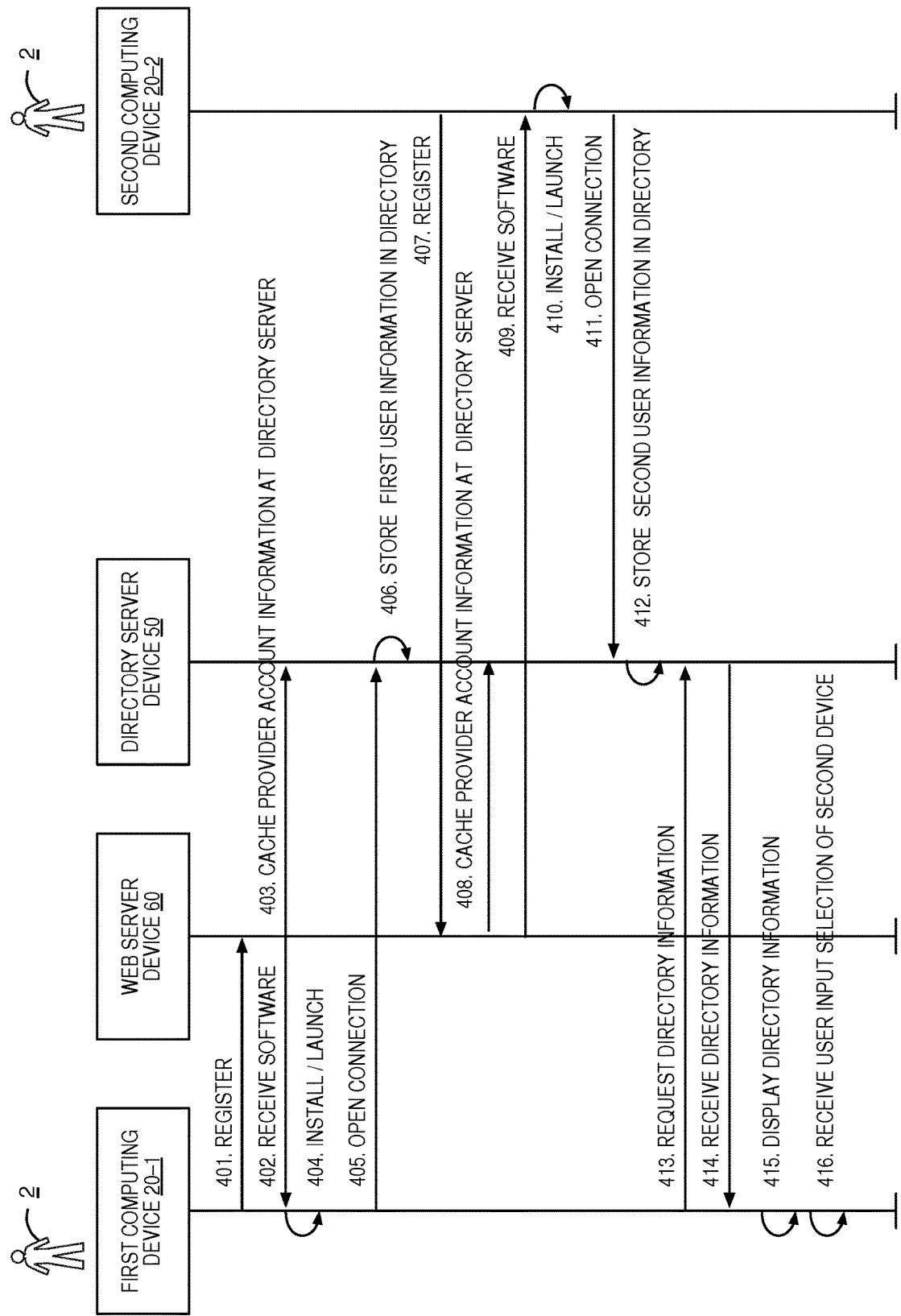
FIG. 4A is a network diagram showing exemplary communications between a first computing device, web server device, web socket server device, and a second computing device when the second computing device is initially offline according to some embodiments.

FIG. 4A illustrates the network diagram for selecting a second computing device that is online to receive a study. The first computing device registers with the Web server device 401. The first computing device receives the software from the web server device 402. Provider account information is sent to the web socket server and cashed. 403. The first computing device installs and launches the downloaded software 404. The first computing device opens a connection with the web socket server device 405. In some embodiments, this connection is accomplished IP network socket. The web socket server stores provider information associated with the first computing device at the web socket server 406. In some embodiments, the provider directory information is comprised of the provider directory information 200 found on FIG. 2A. A second computing device registers with the web server device 407. The provider account information associated with the second computing device is stored at the web socket server 408. The second computing device receives the software download from the Web server device 409. The second computing device installs and launches the downloaded software. A second network connection is opened with the web socket server device to indicate the online availability of the second computing device 411. The web socket server device stores the information regarding the second computing device in the directory 412. The first computing device request directory information from the web socket server 413. The web socket server sends the directory information to the first computing device 414. The first computing device presents the directory information on a display associated with the first computing device 415. The first computing device receives operator input selecting the second computing device 416.

Figure 4B:
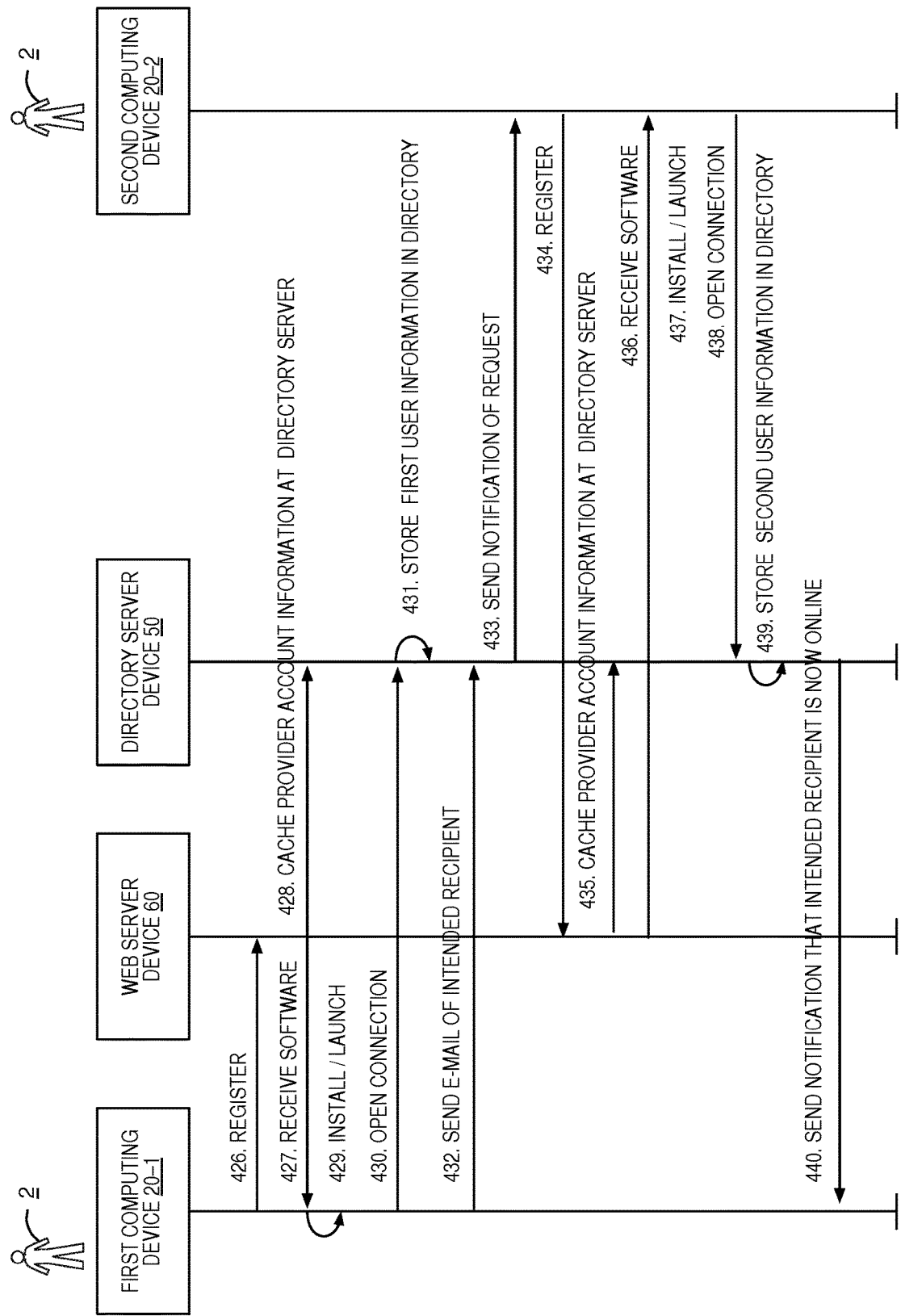
FIG. 4B is a network diagram showing exemplary communications between a first computing device, web server device, web socket server device, and a second computing device when all devices are online according to some embodiments.

FIG. 4B illustrates the network diagram for selecting a second computing device that is offline to receive a study. The first computing device registers with the web server device 426. The first computing device receives the software from the web server device 427. The provider account information corresponding to the first computing device is stored at the web socket server device 428. The first computing device and installs and launches the downloaded software 429. A connection is open between the first computing device and the web socket server device 430. The operator information for the provider associated with the first computing device is stored in the directory 431. The first device sends the email address of the intended recipient to the web socket server 432. A notification of the request is sent from the directory to the potential provider associated with the second computing device 433. The second computing device registers with the web server device 434. The provider account information for the provider corresponding to the second computing device is cached at the web socket server 435. The second computing device receives the software from the web server device 436. The second computing device installs and launches the downloaded software 437, and a connection is opened from the second computing device to the web socket server device 438. The web socket server device stores the provider information corresponding to the second computing device in the directory 439. A notification is sent to the first computing device that the second computing device, corresponding to the intend recipient, is now online 440 and available to interact with and receive studies from the first computing device.

Figure 4C:
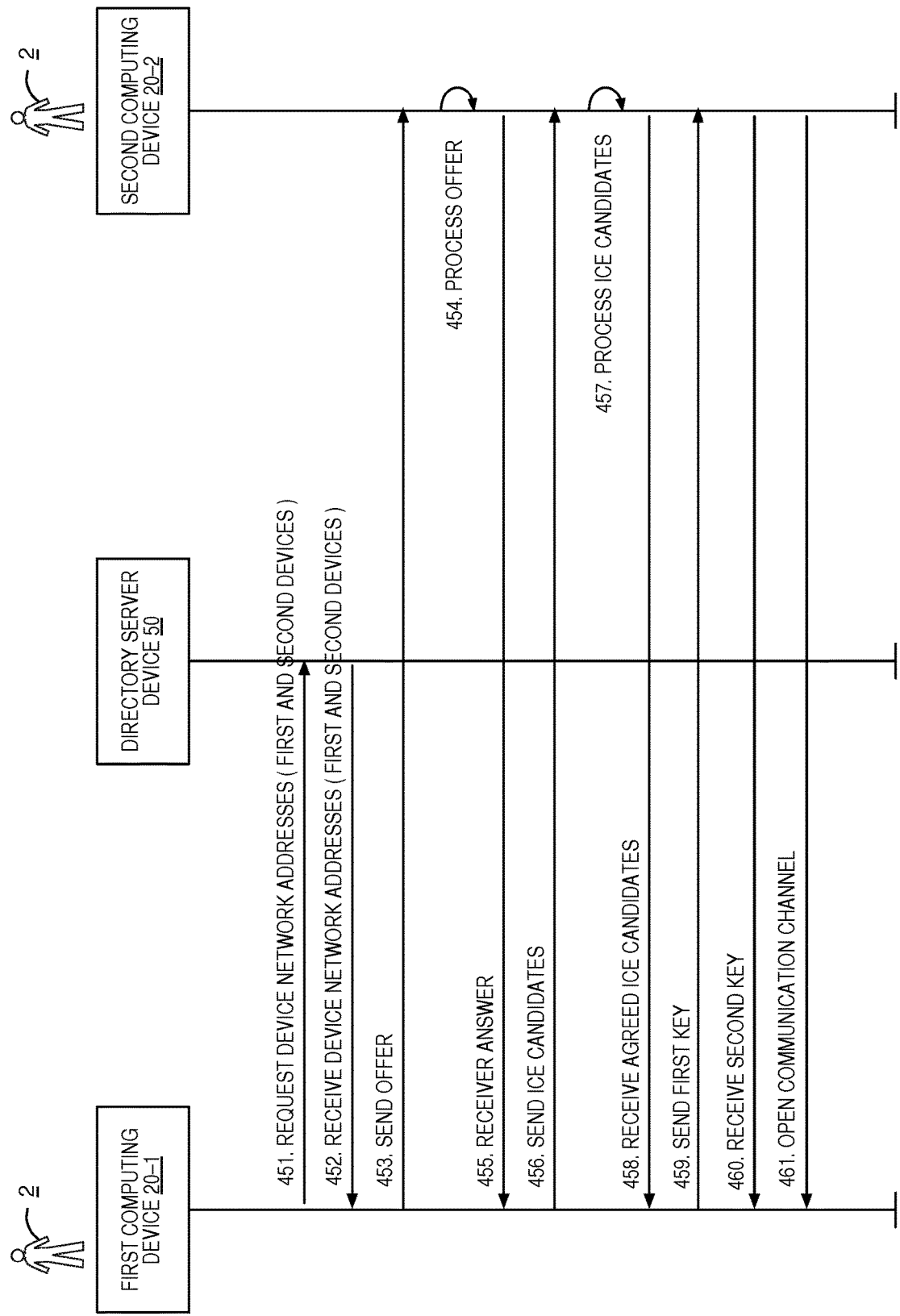
FIG. 4C is a network diagram showing exemplary communications between a first computing device, web socket server device, and a second computing device when opening a secure connection between the first and second computing devices according to some embodiments.

FIG. 4C illustrates a networking diagram for opening a network connection between the first computing device and the second computer device allowing the two devices to communicate. The first computing device sends a request to the web socket server device for the network address of the second computing device 451. The web socket server device responds by sending the requested networking address to the first computing device 452. In some embodiments, such as the embodiment of FIG. 1C, the web socket server device comprises a STUN (Session Traversal of User Datagram Protocol [UDP] Through Network Address Translators [NATs]) server and a TURN (Traversal Using Relays around NAT) server. The STUN server allows clients to find out their public address, the type of NAT they are behind and the internet side port associated by the NAT with a particular local port. This information is used to set up UDP communication between the client and the VoIP provider to establish a call. The STUN protocol is defined in RFC 3489. In response to receiving the request for networking address of the first and second computing devices 451, the STUN operates to determine the public networking address of the first and second computing devices and sends them back to the first computing device 452. In instances where the STUN server fails because the NAT traversal is symmetric, the TURN server is used and the connection is established using TCP instead of the UDP used with the STUN server. Once in possession of the second computing device public network address, the first computing device sends an offer to connect to the second computing device 453. The second computing device processes the offer 454. ICE candidates are sent from the first computer device to the second computing device 456, and processed by the second computing device 457. An acknowledgement is sent to the first computing device 458 indicating the agreed upon ICE candidates. The exchange of ICE candidates allows the first and second device to select the combination that will provide the greatest throughput and the shortest latency. As used herein, ICE stands for Interactive Connectivity Establishment. ICE is a techniques used in NAT (network address translator) for establishing communication for VOIP, peer-peer, instant-messaging, and other kind of interactive media. Typically, an ICE candidate provides information regarding the IP address and port from where the data is going to be exchanged. The first computing device sends a first key to the second computing device, which responds by sending a second key to the first computing device. Once both the first computing device and the second device are in possession of both the first key and the second key a communication channel is opened 461.

Figure 4D:
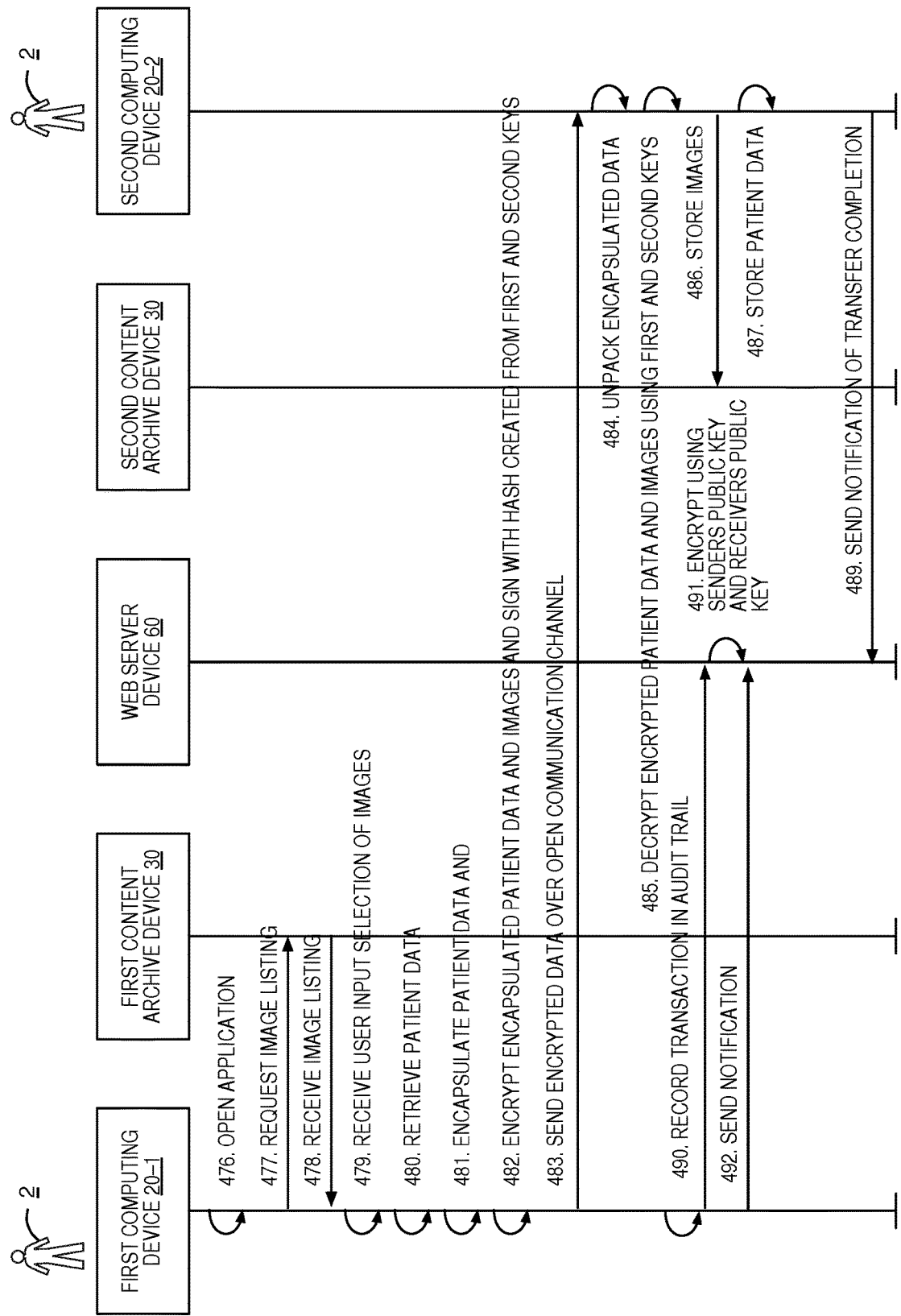
FIG. 4D is a network diagram showing exemplary communications between a first computing device, first content archival device, web socket server device, second content archival device, and a second computing device when transmitting data between the first and second computing devices according to some embodiments.

Now referring to the FIG. 4D, a networking diagram is shown for creating a transmission payload to be sent from the first computing device to the second computing device. The first computing device launches the application and/or browser 476. The first computing device sends a request to the first content archival device requesting an image listing 477, and the first archival device responds by sending the listing 478. The image listing is presented on the display of the first computer device and operator input is received selecting a group of images for inclusion 479. Patient information is retrieved 480, and the image information and patient information is encapsulated 481. In some embodiments, the patient data is comprised of the patient information 220 found in FIG. 2B. Using the first key on the second key the patient information and image information is encrypted 482. A transmission payload is created by attaching a header to the encrypted patient information and image information. The transmission payload is sent from the first computing device to the second computing device 483. Once received, the encapsulated data is subsequently unpacked 484. The second computing device decrypts the encrypted patient information and image information using in the first and second keys 485. The images are stored in the second content archival device 486. The patient information is stored at the second computing device and a record of the transaction is stored in the audit trail 488. Finally, a notification is sent from the web server device 60 to an other device notifying the operator of the other device a transmission payload has been received (not shown). Likewise, the first computing device stores a record of the transaction in the audit trail 490 and a notification is sent to an other device notifying the operator of the other device a transmission payload has been sent.

FIG. 5 is a diagram illustrating the relationships and interactions between computing devices employing endpoints to facilitate the efficient sharing of data from a plurality of communication nodes. In this example, three computing devices 20-[1-3] are operating communication nodes 30-[1-3]. Each computing device 20 is able to view data received from its communications node 30. However, it is not necessarily able to view data from the other communication nodes operating on the LAN. For example, computing device 20-1 operating communications node 30-1 has received data A. Likewise, computing device 20-2 operating communications node 30-2 has received data B and computing device 20-3 operating communications node 30-3 has received data C. However, computing device 20-1 operating communications node 30-1 is necessarily able to view data B and data C. To alleviate this issue, endpoint 80-1 operates to aggregate data A, data B, and data C at the endpoint 80-1. A computing device 20-4 on the local area network is able to view data from a plurality of communications nodes 30[1-3] through accessing only the endpoint 80-1. In another aspect of operation, one or more second endpoints (slaves) 80-2 80-3 operate to mirror some or all data available at a first endpoint (master). In the example of FIG. 5, endpoint 80-2 is mirroring all data present at endpoint 80-1, while endpoint 80-3 is only mirroring data A and C, but not B. This configuration operates to achieve improved performance by load balancing data requests across more than one endpoint. Additionally, the computing device may probe for access latency and throughput from a plurality of endpoints, and chose to access the data from the endpoint that is mirroring the desired data and has the best characteristics in terms of latency and throughput for that particular computing device 20-4. In the example of FIG. 5, computing device 20-4 desires to access data B. Data B is available from endpoints 80-1 and 80-2 but not 80-3. Computing device 20-4 probes endpoint 80-1 and 80-2 and determines that the access times are 10 ms and 5 ms respectively. As such, computing device 20-4 receives data B from endpoint 80-2. In some embodiments, the endpoints may not all be operated at the same geographical location. For example, a provider 4 with more than one office may use endpoints to make data from all of the office available to each of the offices. In some embodiments, network tunneling mechanisms such as VPN may be used to connect the endpoints operating at the individual offices.

FIG. 6 is a block diagram of a computing device according to one embodiment of the present invention. As illustrated, the computing device 20 includes a controller 604 connected to memory 606, one or more communications interfaces 608, one or more operator interface components 610, one or more storage devices 612, and a location module 614 by a bus 602 or similar mechanism. The controller 604 is a microprocessor, digital ASIC, FPGA, or the like. In general, the computing device 20 includes a control system 22 having associated memory 606. In this embodiment, the controller 604 is a microprocessor, and the viewer component 24, browsing component 26, and addressing component 28, communications component 30, communications node 30, encryption component 32, encapsulation component 34, transmission component 36, notification component 38, and audit component 40. are implemented in software and stored in the memory 606 for execution by the controller 604. However, the present invention is not limited thereto. The aforementioned components may be implemented in software, hardware, or a combination thereof. The computing device 20 also includes a communication interface 608 enabling the computing device 20 to connect to the network 15. The one or more user interface components 610 include, for example, a touchscreen, a display, one or more user input components (e.g., a keypad), a speaker, or the like, or any combination thereof. The storage device(s) 612 is a non-volatile memory. In this embodiment, the location module 614 is a hardware component, such as a GPS receiver. However, the present invention is not limited thereto.

FIG. 7 is a block diagram of a content archival device 40 according to one embodiment of the present invention. As illustrated, the content archival device 40 includes a controller 704 connected to memory 706, one or more communications interfaces 708, one or more user interface components 710, one or more storage devices 712 by a bus 702 or similar mechanism. The controller 704 is a microprocessor, digital ASIC, FPGA, or the like. In general, the content archival device 40 includes a control system 42 having associated memory 706. In this embodiment, the controller 704 is a microprocessor, and the and the archival server 44 is implemented in software and stored in the memory 706 for execution by the controller 704. However, the present invention is not limited thereto. The aforementioned functions may be implemented in software, hardware, or a combination thereof. The content archival device 40 also includes a communication interface 708 enabling the content archival device 40 to connect to the network 15. The one or more user interface components 710 include, for example, a touchscreen, a display, one or more user input components (e.g., a keypad), a speaker, or the like, or any combination thereof. The storage device(s) 712 is a non-volatile memory.

FIG. 8 is a block diagram of a web socket server device 50 according to an embodiment of the present invention. As illustrated, web socket server device 50 includes a controller 804 connected to a memory 806, one or more secondary storage devices 812, and one or more communications interfaces 808 by a bus 802 or similar mechanism. The controller 804 is a microprocessor, digital Application Specific Integrated Circuit ASIC, Field Programmable Gate Array FPGA, or the like. In general, the comparison server device 70 includes a control system 72 having associated memory 806. In one embodiment, the controller 804 is a microprocessor, and the provider directory component 53, registration module 54, download module 56, and management console 57 are implemented in software and stored in the memory 806 for execution by the controller 804. However, the present invention is not limited thereto. The aforementioned components and modules may be implemented in software, hardware, or a combination thereof. Further, the provider directory information 200 may be stored in the one or more secondary storage devices 812. The secondary storage devices 812 are digital data storage devices such as, for example, one or more hard disk drives. The comparison server device 70 also includes a communication interface 808 enabling the web socket server device 50 to connect to the network 15.

FIG. 9 is a block diagram of a web server device 60 according to an embodiment of the present invention. As illustrated, web server device 60 includes a controller 904 connected to a memory 906, one or more secondary storage devices 912, and one or more communications interfaces 908 by a bus 902 or similar mechanism. The controller 904 is a microprocessor, digital Application Specific Integrated Circuit ASIC, Field Programmable Gate Array FPGA, or the like. In general, the web server device 60 includes a control system 62 having associated memory 906. In one embodiment, the controller 904 is a microprocessor, and the audit information component 64 is implemented in software and stored in the memory 906 for execution by the controller 904. However, the present invention is not limited thereto. The aforementioned components and modules may be implemented in software, hardware, or a combination thereof. Further, the audit information repository 270 may be stored in the one or more secondary storage devices 912. The secondary storage devices 912 are digital data storage devices such as, for example, one or more hard disk drives. The web server device 60 also includes a communication interface 908 enabling the web server device 60 to connect to the network 15.

FIG. 10 is a block diagram of an endpoint device 80 according to an embodiment of the present invention. As illustrated, endpoint device 80 includes a controller 1004 connected to a memory 1006, one or more secondary storage devices 1012, and one or more communications interfaces 1008 by a bus 1002 or similar mechanism. The controller 1004 is a microprocessor, digital Application Specific Integrated Circuit ASIC, Field Programmable Gate Array FPGA, or the like. In general, the endpoint device 80 includes a control system 82 having associated memory 1006. In one embodiment, the controller 1004 is a microprocessor, and the configuration module 83, discovery module 84, aggregation module 85, mirroring module 86 and response module 87 are implemented in software and stored in the memory 1006 for execution by the controller 1004. However, the present invention is not limited thereto. The aforementioned components and modules may be implemented in software, hardware, or a combination thereof. Further, the aggregated/mirrored data 88 may be stored in the one or secondary storage devices 1012. The secondary storage devices 1012 are digital data storage devices such as, for example, one or more hard disk drives. The endpoint device 80 also includes a communication interface 1008 enabling the endpoint device 80 to connect to the network 15.

In an embodiment, the communication channel initiated between a first device and a second device is periodically closed, and subsequently opened, after initiation. This persistent closing and opening of the communication channel provides an additional level of security for the present invention, as the communication channel is not constantly open and vulnerable to a third-party infiltration or hacking. The closing and opening frequency can be random, or pre-determined by either the first device or the second device, or by the network.

In an embodiment, the communication channel is not completely terminated such that it does not need to be re-initiated in order to be opened after being closed. When closed, an instance remains active, where the instance is not capable of data transfer. In another embodiment, the communication channel is terminated when closed, such that it needs to be re-initiated in order to be opened after being closed. In this embodiment, no instance of the communication channel remains active upon the communication channel being closed.

In an embodiment, the network includes a plurality of devices which are registered or subscribed to the network. All registered devices are able to communicate with each other through the network as described above, via the directly server, or otherwise. Furthermore, a registered device, such as, for example, a medical provider device, may transmit an electronic message to a non-registered device, such as, for example, an out-of-network diagnostic provider device. The term "out-of-network" refers to a device, site, client, or system that is not registered with the network.

The electronic message can be in the form on an email, chat message, social media message, text message, multimedia message, hyperlink, direct message, and the like. The electronic message can include means to access a virtual viewing client, such as a native client, thin client, or web-based client, from the network. When a non-registered device receives the electronic message from the registered device, the non-registered device can access the virtual viewing client via a hyperlink embedded within the electronic message.

Upon launching the virtual viewing client, the non-registered device and the registered device become communicatively linked via a secure communication channel. Thereafter, the registered device may transmit data, such as encrypted data packages, to the non-registered device. The non-registered device can receive, unpack, decrypt, and view the encrypted data packages using the virtual viewing client.

In an embodiment, the virtual viewing client is capable of displaying DICOM images. In a further embodiment, the virtual viewing client is a virtual PACS that allows a user of the non-registered device to edit, manipulate, and annotate the received data. The virtual PACS can also automatically integrate with a local PACS on the non-registered device in order to transfer data to the non-registered device user's local PACS.

The electronic message can also include means for allowing the non-registered device to register and/or subscribe to the network, so that the non-registered device can become a registered device. For example, the electronic message may include an embedded link to a web-based registration server, form, website, or secure portal where the user of the non-registered device can input registration information, such as their name, identifier, machine name, location, contact information, etc.

In an embodiment, the user of the non-registered device may be asked to enter financial information, such as credit card, bank account, wire transfer, or direct debit information, in order to register the non-registered device with the network. The user of the non-registered device may be asked to authorize a one-time registration fee, or alternatively, a recurring fee that is charged on a periodic basis, such as, for example, weekly, monthly, quarterly, etc., or which is charged based on data transfer usage, such as, for example, by file size, facility size, number of users, bandwidth usage, per each transfer session, etc.

In yet another embodiment, upon launching the virtual viewing client, the non-registered device may automatically be registered with the network by transmitting electronic identifying information to the network.

The present invention is not limited to use within a medical environment, and the invention may be used to directly and securely transfer financial, military, video, multimedia, audio, personally identifiable, and other sensitive information between to remote locations without storing the data on an intermediary server, thereby allowing a direct transfer of encrypted data irrespective of the content-type, and without utilizing the intermediary server for storage of the transmitted data.

In an embodiment, the server verifies the connections on the network using a MySQL relational database. The present invention initiates connections and issues networking information through, for example, a Web Socket server that verifies connections by referencing a MySQL relational database comprising of entities (such as, for example, individuals, groups, medical providers, diagnostic providers, etc.) verified in, for example, a patient's continuum of care. The server is capable of storing an audit trail related to the encrypted data package, as described above.

In another embodiment, the first device and the second device each write data for the audit trail into the same record. However, once the audit trail is written, neither the first device nor the second device can access the audit trail, and the audit trail is partitioned into separate databases within the server, where data containing protected health information and/or personally identifiable information is stored in a separate database from data that does not contain such information. Databases contained the protected health information or personally identifiable information is not accessible by the first device or the second device, and this information is only accessible to an end user who has an independently maintained encryption key.

Furthermore, the server itself cannot access the audit trail. It does not matter whether or not a device has stored information into the audit trail. No device has access to read the audit trail, but any device verified in a connection has access to write to the audit trail. No device has access to the corresponding audit trail record. Only an end user with the independent encryption key has access.

In an embodiment, the communication channel initiated between a first device and a second device is periodically closed, and subsequently opened, after initiation. For example, connections persist for the duration of a data exchange, unless the data exchange exceeds a timeout on the Web Socket server or exceeds the time between end client maintenance restarts. Maintenance restarts on the end user client, which occur on average twice a day, or which are programmatically required in order to confirm that idle connections are completely destroyed.

This recurring closing and opening of the communication channel provides an additional level of security for the present invention, as the communication channel is not constantly open and vulnerable to a third-party infiltration or hacking. The closing and opening frequency can be random, or pre-determined by either the first device or the second device, or by the network.

In an embodiment, the communication channel is not completely terminated such that it does not need to be re-initiated in order to be opened after being closed. When closed, an instance remains active, where the instance is not capable of data transfer. In another embodiment, the communication channel is terminated when closed, such that it needs to be re-initiated in order to be opened after being closed. In this embodiment, no instance of the communication channel remains active upon the communication channel being closed.

During a maintenance restart of an end user device, such as an Imagex device, or a network system, such as the Medicom Imagex On-Site Windows Service VM, the connection is completely terminated, and has be re-initiated in order to be opened again. Complete re-initiation is required after a maintenance restart, which happens on average twice a day for each Imagex client. Connections are completely terminated in this case, and are partially terminated in the other. Web socket time-outs and maintenance restarts completely terminate connections, otherwise the connection is idle and unusable, but not entirely terminated.

In an embodiment, the network includes a plurality of devices that are registered or subscribed to the network. All registered devices are able to communicate with each other through the network as described above, via the directly server, or otherwise. Furthermore, a registered device, such as, for example, a medical provider device, may transmit an electronic message to a non-registered device, such as, for example, an out-of-network diagnostic provider device. The term "out-of-network" refers to a device, site, client, or system that is not registered with the network.

The electronic message can be in the form on an email, chat message, social media message, text message, multimedia message, hyperlink, direct message, and the like. The electronic message can include means to access a virtual viewing client, such as a native client, thin client, or web-based client, from the network. When a non-registered device receives the electronic message from the registered device, the non-registered device can access the virtual viewing client via a hyperlink embedded within the electronic message.

Upon launching the virtual viewing client, the non-registered device and the registered device become communicatively linked via a secure communication channel. Thereafter, the registered device may transmit data, such as encrypted data packages, to the non-registered device. The non-registered device can receive, unpack, decrypt, and view the encrypted data packages using the virtual viewing client.

In an embodiment, the virtual viewing client is capable of displaying DICOM images. In a further embodiment, the virtual viewing client is a virtual PACS that allows a user of the non-registered device to edit, manipulate, and annotate the received data. The virtual PACS can also automatically integrate with a local PACS on the non-registered device in order to transfer data to the non-registered device user's local PACS.

The electronic message can also include means for allowing the non-registered device to register and/or subscribe to the network, so that the non-registered device can become a registered device. For example, the electronic message may include an embedded link to a web-based registration server, form, website, or secure portal where the user of the non-registered device can input registration information, such as their name, identifier, machine name, location, contact information, etc.

In an embodiment, the user of the non-registered device may be asked to enter financial information, such as credit card, bank account, wire transfer, or direct debit information, in order to register the non-registered device with the network. The user of the non-registered device may be asked to authorize a one-time registration fee, or alternatively, a recurring fee that is charged on a periodic basis, such as, for example, weekly, monthly, quarterly, etc., or which is charged based on data transfer usage, such as, for example, by file size, facility size, number of users, bandwidth usage, per each transfer session, etc.

In yet another embodiment, upon launching the virtual viewing client, the non-registered device may automatically be registered with the network by transmitting electronic identifying information to the network.

The present invention is not limited to use within a medical environment, and the invention may be used to directly and securely transfer financial, military, video, multimedia, audio, personally identifiable, and other sensitive information between to remote locations without storing the data on an intermediary server, thereby allowing a direct transfer of encrypted data irrespective of the content-type, and without utilizing the intermediary server for storage of the transmitted data.

For example, in an embodiment, the present invention may be implemented within a social network, where users can send encrypted messages and data using the communication channel, without storing the transmitted data on any social network server or storage medium. Users wishing to send such data to a non-user of the social network may send a message as described above, where the non-user is presented with a viewing client and an opportunity to join the social network via the message.

Those skilled in the art will recognize improvements and modifications to the embodiments of the present invention. All such improvements and modifications are considered within the scope of the concepts disclosed herein and the claims that follow.

What is claimed is:

1. A system for retrieving medical data through a web-based portal, comprising:
   a recipient device launching the web-based portal;
   a sending device storing the medical data, wherein the medical data consists of both medical images and medical reports,
   wherein the sending device encapsulates the medical images and medical reports into a single file, wherein the single file is encrypted using 2048 RSA keys, and wherein the sending device transmits a hyperlink to the web-based portal;
   a peer-to-peer communication channel facilitating the transmission of the single file from the sending device to the web-based portal, wherein the communication channel is created using 2048 Datagram Transport Layer Security,
   wherein selection of the hyperlink by a user causes the single file to be transmitted from the sending device to the web-based portal via the peer-to-peer communication channel; and
   a medical image viewer displaying the medical images upon receipt of the single file at the recipient device,
   wherein an audit trail related to the transmission of the single file is encrypted and stored on a third-party server, and wherein the audit trail accessible by the recipient device or the sending device using an encryption key,
   wherein the sending device and the web-based portal exchange Interactive Connectivity Establishment (ICE) candidates in order to select data transfer protocols that provide the greatest throughput and the shortest latency over the peer-to-peer communication channel, and
   wherein the web-based portal displays a dashboard having a status of outgoing transmissions of medical data to multiple recipient devices and a status of incoming transmissions of medical data from sending devices in a side-by-side fashion on a single screen.

2. The system of claim 1, wherein the medical images, medical reports and the medical image viewer are encapsulated into the single file.

3. The system of claim 1, wherein the sending device encrypts the single file using 2048 RSA keys prior to transmitting the single file to the web-based portal.

4. The system of claim 3, wherein the web-based portal decrypts the single file prior to the medical images being displayed by the medical image viewer.

5. The system of claim 1, wherein the hyperlink is transmitted from the sending device to the web-based portal via a server that is not communicatively coupled to the peer-to-peer communication channel.

6. A method for retrieving medical data through a web-based portal, comprising:
   transmitting, by a sending device, a hyperlink to a web-based portal launched on a recipient device;
   displaying the hyperlink within the web-based portal;
   initiating a peer-to-peer communication channel upon selection of the hyperlink, wherein the peer-to-peer communication channel facilitates the transmission of the medical data from the sending device to the recipient device, wherein the medical data consists of both medical images and medical reports, and wherein the communication channel is created using 2048 Datagram Transport Layer Security;
   writing, by the sending device and recipient device, audit data related to the transmission of the medical data, to an audit trail stored on a third-party server, wherein the sending device and the recipient device cannot read the audit trail within an encryption key; and
   displaying the medical images on a medical viewer,
   wherein the medical images and medical reports are encapsulated into a single file prior to transmission by the sending device, wherein the single file is encrypted by the sending device using 2048 RSA keys,
   wherein the sending device and the web-based portal exchange Interactive Connectivity Establishment (ICE) candidates in order to select data transfer protocols that provide the greatest throughput and the shortest latency over the peer-to-peer communication channel, and
   wherein the web-based portal displays a dashboard having a status of outgoing transmissions of medical data to multiple recipient devices and a status of incoming transmissions of medical data from sending devices in a side-by-side fashion on a single screen.

7. The method of claim 6, wherein the medical images, medical reports, and the medical image viewer are encapsulated into the single file.

8. The method of claim 6, wherein the third-party server partitions personally identifiable information and non-personally identifiable information within the audit trail onto separate databases.

9. The method of claim 8, wherein the web-based portal decrypts the single file prior to the medical images being displayed by the medical image viewer.

10. The method of claim 6, wherein the hyperlink is transmitted from the sending device to the web-based portal via a server that is not communicatively coupled to the peer-to-peer communication channel.

11. A system for retrieving medical data through a web-based portal, comprising:
- a recipient device launching the web-based portal;
- a sending device storing the medical data, wherein the medical data consists of both medical images and medical reports,
- wherein the sending device transmits a hyperlink to the web-based portal, and
- wherein the sending device encapsulates the medical images and medical reports into a single file, wherein the single file is encrypted using 2048 RSA keys;
- a medical image viewer;
- a third-party server storing an audit trail related to the transmission of the single file, the audit trail capable of being written to by the sending device and the recipient device, and the audit trail not capable of being read by the sending device and recipient device without an encryption key; and
- a peer-to-peer communication channel facilitating the transmission of the single file from the sending device to the web-based portal, wherein the communication channel is created using 2048 Datagram Transport Layer Security,
- wherein the web-based portal displays the hyperlink, and wherein the web-based portal decrypts the single file prior to the medical images being displayed by the medical image viewer,
- wherein selection of the hyperlink by a user causes the single file to be transmitted from the sending device to the web-based portal via the peer-to-peer communication channel, and
- wherein the sending device and the web-based portal exchange Interactive Connectivity Establishment (ICE) candidates in order to select data transfer protocols that provide the greatest throughput and the shortest latency over the peer-to-peer communication channel, and
- wherein the web-based portal displays a dashboard having a status of outgoing transmissions of medical data to multiple recipient devices and a status of incoming transmissions of medical data from sending devices in a side-by-side fashion on a single screen.

12. The system of claim 11, wherein medical images, medical reports and the medical image viewer are encapsulated into the single file.

13. The system of claim 11, wherein the hyperlink is transmitted from the sending device to the web-based portal via a server that is not communicatively coupled to the peer-to-peer communication channel.

* * * * *